United States Patent
Meadows et al.

(10) Patent No.: US 8,677,541 B2
(45) Date of Patent: Mar. 25, 2014

(54) ORAL CARE PRODUCTS AND METHODS OF USING AND MARKING THE SAME

(71) Applicant: The Gillette Company, Boston, MA (US)

(72) Inventors: Mark Stephen Meadows, Boston, MA (US); Jose Tadeo Vergara de Castro, Newton, MA (US); Mark Edward Farrell, Medfield, MA (US); William Ralph Brown, Jr., Peabody, MA (US); Eric V. Borges, Plymouth, MA (US); Long Sheng Yu, South Grafton, MA (US)

(73) Assignee: Braun GmbH, Kronberg (DE)

( * ) Notice: Subject to any disclaimer, the term of this patent is extended or adjusted under 35 U.S.C. 154(b) by 0 days.

(21) Appl. No.: 13/626,127

(22) Filed: Sep. 25, 2012

(65) Prior Publication Data

US 2013/0055513 A1  Mar. 7, 2013

Related U.S. Application Data

(63) Continuation of application No. 12/559,663, filed on Sep. 15, 2009, now abandoned.

(51) Int. Cl.
  *A46B 3/22* (2006.01)
  *A61H 13/00* (2006.01)
(52) U.S. Cl.
  USPC ............ 15/22.1; 15/167.1; 15/167.2; 15/188; 15/207.2; 601/141; 601/142
(58) Field of Classification Search
  USPC ......... 15/22.1, 167.1, 167.2, 187, 188, 207.2; 601/139, 141, 142
  See application file for complete search history.

(56) References Cited

U.S. PATENT DOCUMENTS

| | | | |
|---|---|---|---|
| 1,776,312 A | | 9/1930 | Czencz |
| 1,818,146 A | | 8/1931 | Maker |
| 2,016,597 A | | 10/1935 | Drake |
| 2,140,294 A | | 12/1938 | Loeffler |
| 2,160,731 A | | 5/1939 | Haeberlin |
| 2,176,309 A | * | 10/1939 | Love et al. .................... 601/141 |
| 2,317,485 A | | 4/1940 | Rider |
| 2,206,726 A | * | 7/1940 | Lasater .......................... 15/188 |
| 2,250,112 A | | 7/1941 | Larson |
| 2,257,709 A | | 9/1941 | Anderson |
| 2,607,064 A | * | 8/1952 | Sullivan et al. ................. 15/187 |
| 2,876,477 A | | 3/1959 | Stewart |
| 2,917,057 A | * | 12/1959 | Busseuil ....................... 401/129 |
| 3,103,027 A | | 9/1963 | Birch |
| D196,635 S | | 10/1963 | Kinsella |
| 3,163,874 A | | 1/1965 | Bauer |
| 3,217,074 A | | 11/1965 | Gould et al. |
| 3,302,230 A | | 2/1967 | Poppelman |

(Continued)

OTHER PUBLICATIONS www.SkyMall.com—The 40 second electric toothbrush.

*Primary Examiner* — Mark Spisich
(74) *Attorney, Agent, or Firm* — John P. Colbert

(57) ABSTRACT

An oral care implement may include a base portion sized for insertion into an oral cavity and a plurality of flexible, elastomeric elements extending from the base portion, wherein each of the plurality of flexible, elastomeric elements comprises an edge, wherein at least one of the edges comprises a micro edge, and wherein the plurality of flexible, elastomeric elements comprises an element density of less than about 5 mm.

14 Claims, 22 Drawing Sheets

(56) References Cited

U.S. PATENT DOCUMENTS

| | | |
|---|---|---|
| 3,335,715 A | 8/1967 | Sexton |
| 3,411,979 A | 11/1968 | Lewis, Jr. |
| 3,527,218 A | 9/1970 | Westline |
| D221,272 S | 7/1971 | Splaine |
| 3,769,652 A | 11/1973 | Rainer |
| 3,823,710 A | 7/1974 | Borden |
| 3,874,084 A | 4/1975 | Cole |
| 3,908,642 A | 9/1975 | Vinmont |
| 4,011,616 A | 3/1977 | Kennedy |
| 4,059,101 A | 11/1977 | Richmond |
| 4,106,501 A | 8/1978 | Ozbey et al. |
| 4,123,844 A | 11/1978 | Kurz |
| 4,224,710 A | 9/1980 | Solow |
| 4,237,574 A | 12/1980 | Kelly et al. |
| 4,325,392 A | 4/1982 | Iten et al. |
| 4,346,492 A | 8/1982 | Solow |
| 4,538,315 A | 9/1985 | Barth |
| 4,612,944 A | 9/1986 | Bachrach et al. |
| 4,612,945 A | 9/1986 | Bachrach |
| 4,795,347 A | 1/1989 | Maurer |
| 4,807,652 A | 2/1989 | Bachrach |
| 4,828,420 A | 5/1989 | Otsuka et al. |
| 4,991,570 A | 2/1991 | Bullard |
| 5,000,684 A | 3/1991 | Odrich |
| 5,040,260 A * | 8/1991 | Michaels ............... 15/167.1 |
| 5,104,315 A | 4/1992 | McKinley |
| 5,175,901 A | 1/1993 | Rabinowitz |
| 5,177,827 A | 1/1993 | Ellison |
| 5,327,608 A * | 7/1994 | Kosakewich ............ 15/22.1 |
| 5,337,435 A | 8/1994 | Krasner et al. |
| 5,339,832 A | 8/1994 | Kittelsen et al. |
| 5,355,546 A | 10/1994 | Scheier et al. |
| 5,365,624 A | 11/1994 | Berns |
| 5,483,722 A | 1/1996 | Scheier et al. |
| 5,491,865 A | 2/1996 | Gueret |
| 5,500,970 A | 3/1996 | Maurer et al. |
| 5,615,443 A | 4/1997 | Lai |
| 5,876,206 A | 3/1999 | Maurer |
| 5,896,614 A | 4/1999 | Flewitt |
| 5,921,255 A | 7/1999 | Garita |
| 5,930,861 A | 8/1999 | White |
| 6,003,525 A | 12/1999 | Katz |
| 6,067,684 A | 5/2000 | Kweon |
| 6,085,761 A | 7/2000 | Inaba |
| 6,138,310 A | 10/2000 | Porper et al. |
| 6,138,314 A | 10/2000 | Schiff et al. |
| 6,223,376 B1 | 5/2001 | Lee |
| 6,254,390 B1 * | 7/2001 | Wagner ............... 433/216 |
| 6,353,956 B1 | 3/2002 | Berge |
| 6,402,768 B1 | 6/2002 | Libel |
| 6,421,867 B1 | 7/2002 | Weihrauch |
| 6,453,501 B1 | 9/2002 | Bella |
| 6,553,604 B1 | 4/2003 | Braun et al. |
| 6,554,614 B1 | 4/2003 | Dubbe et al. |
| 6,609,910 B2 | 8/2003 | Narayanan |
| 6,893,259 B1 | 5/2005 | Reizenson |
| 7,020,928 B2 | 4/2006 | Hohlbein |
| 7,044,737 B2 | 5/2006 | Fu |
| 7,118,377 B2 | 10/2006 | Inoue et al. |
| 7,143,462 B2 | 12/2006 | Hohlbein |
| 2003/0088932 A1 | 5/2003 | Gardiner |
| 2003/0088935 A1 | 5/2003 | Favagrossa |
| 2003/0196283 A1 | 10/2003 | Eliav et al. |
| 2003/0205234 A1 | 11/2003 | Bardach et al. |
| 2003/0229959 A1 | 12/2003 | Gavney, Jr. et al. |
| 2004/0074035 A1 | 4/2004 | Huang |
| 2004/0255416 A1 | 12/2004 | Hohlbein |
| 2005/0138742 A1 | 6/2005 | Jaszenovics et al. |
| 2005/0166344 A1 | 8/2005 | Hohlbein et al. |
| 2005/0196725 A1 | 9/2005 | Fu |
| 2005/0210612 A1 | 9/2005 | Hohlbein et al. |
| 2006/0078844 A1 | 4/2006 | Goldman et al. |
| 2006/0162108 A1 * | 7/2006 | Georgi et al. ............ 15/167.1 |
| 2007/0101525 A1 | 5/2007 | Hohlbein |
| 2007/0199168 A1 | 8/2007 | Blanchard et al. |
| 2008/0184511 A1 | 8/2008 | Brown et al. |
| 2008/0199830 A1 | 8/2008 | Fontenot et al. |
| 2009/0211047 A1 * | 8/2009 | Chen ..................... 15/207.2 |

* cited by examiner

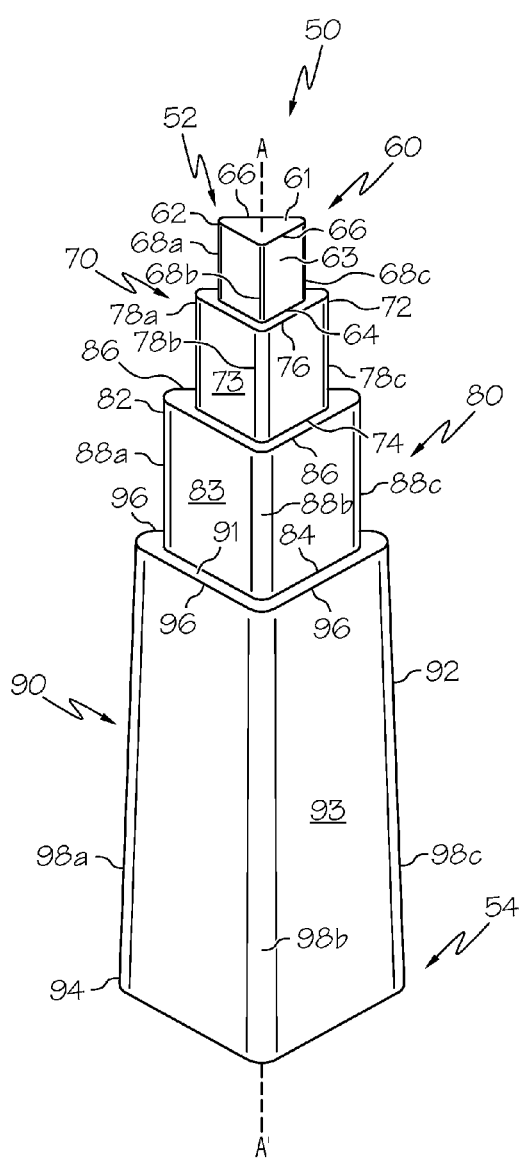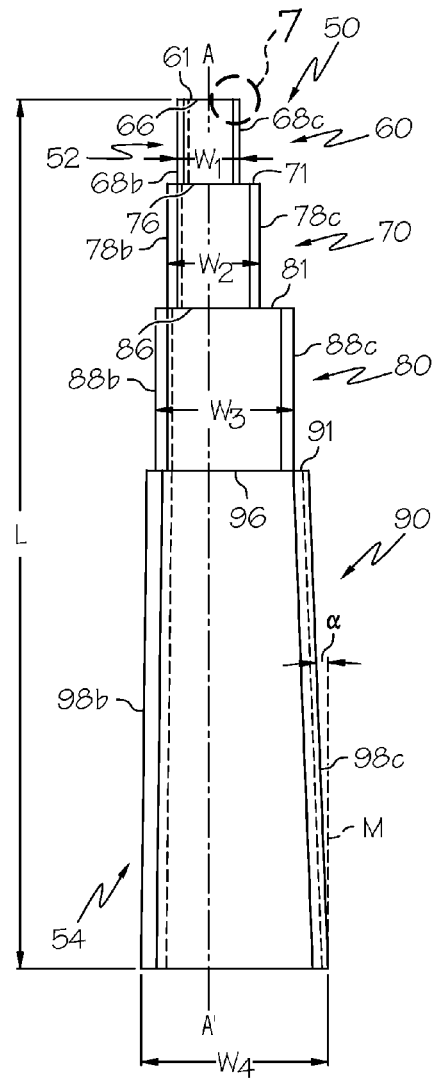
FIG. 4
FIG. 5

ORAL CARE PRODUCTS AND METHODS OF USING AND MARKING THE SAME

This application is a continuation of U.S. application Ser. No. 12/559,663, filed 15 Sep. 2009, now abandoned.

FIELD OF THE INVENTION

The present invention relates to Oral care cleaning implements, devices, and systems having flexible elements, particularly flexible, elastomeric elements, and methods of using and making the same.

BACKGROUND OF THE INVENTION

Although many innovations have been made in the field of oral health care, there is a continuing need for oral care products and methods which can improve the health and appearance of the oral cavity and teeth, such as teeth cleaning, teeth whitening, and plaque removal.

SUMMARY OF THE INVENTION

The several embodiments presented herein are directed to oral care systems and/or oral care implements comprising a base and a plurality of flexible, elastomeric elements, and methods of using and making the same.

One embodiment may comprise an oral care implement that includes, at least in part, a base portion sized for insertion into an oral cavity a plurality of flexible, elastomeric elements extending from the base portion, wherein each of the plurality of flexible, elastomeric elements comprises an edge, at least one of the edges comprises a micro edge, and the plurality of flexible, elastomeric elements comprises an element density of less than about 5 mm.

Another embodiment may comprise an oral care implement that includes, at least in part, a base portion sized for insertion into an oral cavity and a plurality of flexible, elastomeric elements extending from the base portion, wherein at least one of the plurality of flexible, elastomeric elements comprises a first section having a first section edge and a first transverse cross sectional area, and wherein a second section disposed adjacent to the first section along a longitudinal axis of the at least one of the plurality of flexible, elastomeric elements. The second section includes a second section edge and a second transverse cross sectional area different from the first transverse cross sectional area.

Yet another embodiment may comprise an oral care implement that includes, at least in part, a base portion sized for insertion into an oral cavity, the base portion having a base wall and two opposed, side walls connected to the base wall that form a channel for receiving teeth within an oral cavity, and a plurality of flexible, elastomeric elements extending into the channel from the base and two opposed, side walls. Each of the plurality of flexible, elastomeric elements comprises an edge and a longitudinal axis, wherein at least one of the plurality of flexible, elastomeric elements comprises a first section having a first transverse cross sectional area and a second section having a second transverse cross sectional area that is disposed adjacent to the first section along the longitudinal axis of the at least one flexible, elastomeric element, and wherein the second transverse cross sectional area is different than the first transverse cross sectional area.

Still yet another embodiment may comprise a method of forming a micro edge of an flexible, elastomeric element. The method may include the steps of forming a mold cavity with a first mold plate and a second mold plate positioned adjacent to the first mold plate, forming a mold corner of the mold cavity using an intersection of the first mold plate and second mold plate, injecting an elastomer into the mold cavity, and allowing gas contained within the mold cavity to out-gas through the intersection between the first and second mold plates to form a micro edge along the mold corner formed by the intersection.

BRIEF DESCRIPTION OF THE DRAWINGS

While the specification concludes with claims particularly pointing out and distinctly claiming the invention, it is believed the same will be better understood from the following description taken in conjunction with the accompanying drawings in which:

FIG. 4 is a perspective view of a flexible, elastomeric element of the oral care implement of FIG. 3;
FIG. 5 is a side elevational view of the flexible, elastomeric element of FIG. 4.

DETAILED DESCRIPTION OF THE INVENTION

Figure 1A:
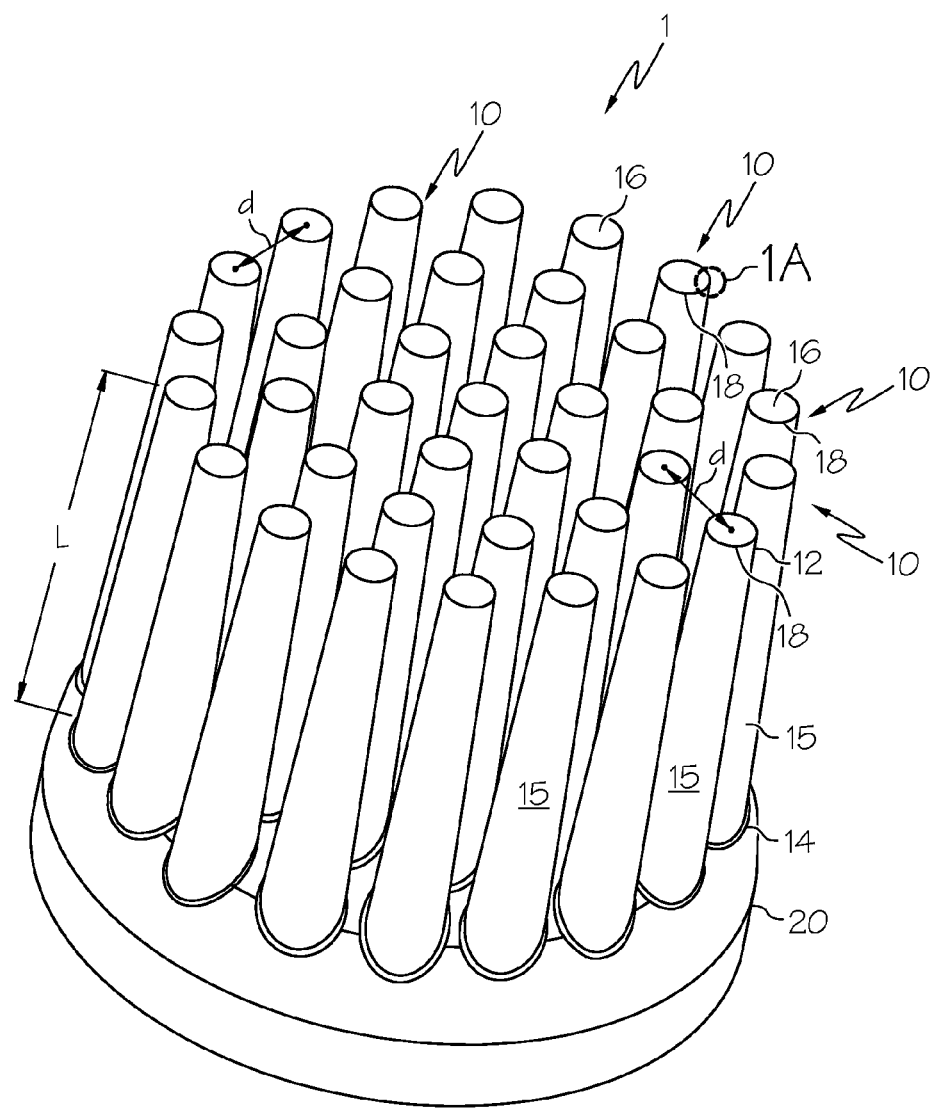
FIG. 1A is a perspective view of an oral care implement.

As used herein, "an edge" is a line at which two surfaces intersect, or a border at which a surface terminates.

"Include" and its variants are non-limiting in the sense that recitation of items "included" in a list does not exclude other items.

As used herein, a "micro" edge is an edge as defined herein that is fabricated to have a tip radius (R) of less than 0.0254 mm, particularly less than or equal to about 0.02 mm, more particularly less than or equal to about 0.015 mm, more particularly less than or equal to about 0.01 mm, more particularly less than or equal to about 0.008 mm, more particularly less than or equal to about 0.0075 mm, more particularly less than or equal to about 0.007 mm, more particularly less than or equal to about 0.0065 mm, more particularly less than or equal to about 0.006 mm, more particularly less than or equal to about 0.0055 mm, more particularly less than or equal to about 0.005 mm, more particularly less than or equal to about 0.0045 mm, more particularly less than or equal to about 0.004 mm, more particularly less than or equal to about 0.0035 mm, more particularly less than or equal to about 0.003 mm, more particularly less than or equal to about 0.0025 mm, more particularly less than or equal to about 0.002 mm, more particularly less than or equal to about 0.0015 mm, more particularly less than or equal to about 0.001 mm, and/or from about 0.0254 mm to about 0.001 mm, from about to 0.02 mm to about 0.001 mm, particularly from about 0.015 mm to about 0.0015 mm, particularly from about 0.01 mm to about 0.002 mm, more particularly from about 0.009 mm to about 0.0025 mm, more particularly from about 0.0085 mm to about 0.0025 mm, and/or more particularly from about 0.008 mm to about 0.0025 mm. One example of a micro edge comprises an out-gassed edge. As used herein, "an out-gassed" edge is an edge, as defined herein, formed by the out-gassing between two cavity mold plates (at the point of engagement between the two cavity mold plates) from a mold cavity used in a molding process such as plastic injection molding. The molding plates are used to form at least a portion of a mold cavity to form an element (e.g., element 10). During the molding process, gas in the mold cavity out-gasses through and between the space located where the two molding plates engage one another (i.e., intersection of the two molding plates), thus pushing and/or pulling the material (e.g., plastic) deep into the corner of the mold cavity formed by the intersection of the two molding plates. When the plastic penetrates into the corner of the mold cavity by the out-gassing process, it forms a micro edge (e.g., micro edge 18) along the flexible element (e.g., element 10).

"Oral care composition" or "oral composition" means a product which in the ordinary course of usage can be retained in the oral cavity for contacting selected dental surfaces and/or oral tissues for purposes of oral activity. In addition to cleaning teeth to remove dental plaque, oral care compositions may be used to prevent formation of dental calculus and disorders such as caries, periodontitis and gingivitis, and also to eliminate and prevent oral malodor or halitosis and staining. Some examples of oral care product forms are toothpastes, dentifrices, tooth gels, subgingival gels, foams, mouth rinses, denture products, mouth sprays, lozenges, chewable tablets or chewing gums and strips or films for direct application or attachment to oral surfaces including any hard or soft oral tissues.

As used herein, "oral cavity" means a cavity comprising oral cavity tissue as defined herein, including but not limited to human mouths and/or mouths of other animals.

As used herein, "oral cavity tissue" means any hard or soft tissue disposed within the oral cavity such as teeth and gum tissue.

As used herein, the terms "oral condition" and "condition" are used to refer to dental plaque, tartar, debris, tooth decay, bio films, soft tissue abnormalities, soft tissue lesions, etc. within the oral cavity.

"Orally acceptable additive" means any additive which is now known, or hereinafter becomes known, as a safe and effective additive for an oral care composition. Examples include conventional additives in oral care compositions including but not limited to fluoride ion sources, anti-calculus or anti-tartar agents, desensitizing agents, teeth whitening agents such as peroxide sources, abrasives such as silica, herbal agents, chelating agents, buffers, anti-staining agents, alkali metal bicarbonate salts, thickening materials, humectants, water, surfactants, titanium dioxide, flavor system, sweetening agents, xylitol, coloring agents, and mixtures thereof.

As used herein, the terms "plaque" and "dental plaque" are used to refer to a bio-film that builds up on teeth, on gingival tissue, oral hard tissue, and/or oral soft tissue.

"Plaque bacteria" means bacteria that causes plaque to form.

"Teeth" refers to one or more natural teeth as well as one or more artificial teeth or dental prosthesis.

Referring to FIGS. 1-24, several embodiments of flexible elements (e.g., flexible elements 10, 50, 150, 155, etc.), oral care implements (e.g., implements 1, 20, 2000, etc.) including such elements, and methods of making and using the same are shown. Not to be limited by theory, it has been discovered that the manipulation of certain, but not all, element and/or oral care implement properties provide improved oral care cleaning benefits, including but not limited to reduced cleaning times, increased contact stress, increased contact traces, and plaque removal. One or more of the following flexible element properties: size, cross sectional shape, length, material properties (e.g., hardness (durometer), surface friction, etc.), distance from the oral care tissue (e.g., teeth, gums, etc.), driving motion (i.e., motion initiated on the flexible elements for cleaning of the oral care tissue), and/or edge properties, including but not limited to edge tip radius, number, location, orientation, and hardness/stiffness, may be manipulated or maximized to provide surprisingly improved cleaning of oral care tissue such as, for example, cleaning within interdental areas (i.e., between the teeth). In addition, it has been discovered that the density of flexible elements along an oral care implement that includes such flexible elements when combined with one or more of the flexible element properties set forth above may be maximized to provide improved or optimized cleaning of oral care tissue.

As one example, it has been discovered that manipulating one or more of the element and/or oral care implement properties set forth above impact the contact trace (i.e., the path along a tooth's surface that an edge (cleaning edge) of a flexible element contacts the tooth during the cleaning motion). As such, and not to be limited by theory, with the right combination of properties, it has been discovered that the contact trace of one or more of the flexible elements of an oral care element may be controlled, improved, and/or increased, particularly within the interdental areas, and thus improve the cleaning capabilities of such oral care element(s) and/or implement such as, for example, improved interdental cleaning.

Again, not to be limited by theory, it has been discovered that the contact stress (i.e., the component of the applied force of the flexible element which is normal to the surface of the oral care tissue (tooth or gums) at the point where the edge contacts the oral care tissue divided by the contact area between the edge of the flexible element and the oral care tissue) of one or more of the flexible elements of an oral care implement may be controlled, improved, and/or increased by manipulating the element's edge tip radius, length, spacing with adjacent elements (element density), hardness (durometer), and/or surface friction. It has been discovered that an improved cleaning edge/element configuration can produce high contact stresses over large contact traces (tooth surface areas) for particular cleaning motions.

The several embodiments shown and described herein are examples of flexible elements and/or oral care cleaning implements that provide such improved oral cleaning benefits.

Referring to FIG. 1a, an embodiment of an oral care implement 1 is shown, comprising, in part, a base 20 and a plurality of elements 10 extending from the base 20. Each element 10 may comprise a distal end 12, a proximal end 14 opposite of the distal end 12, a longitudinal axis A-A', and a transverse surface 16 that is disposed transverse to the longitudinal axis A-A'. It is understood that in an element having a different transverse cross sectional shape than element 10 shown in FIG. 1A, the edge 18, rather than being a transverse edge, may be a longitudinal edge, i.e., disposed substantially along the longitudinal axis A-A'. In the embodiment shown, the base 20 and the plurality of elements 10 are fabricated as one integrated unit. It is understood that the base 20 and the plurality of elements 10 may be two separate components that are connected together using conventional techniques and methods of connection such as, for example, adhesives, knotting, sonic welding, etc.

The oral care implement 1 may comprise an implement density of the plurality of elements 10, which comprises the spacing between each adjacent element 10. As such, the element density may be measured by measuring the distance (d) between a center point of one element 10 to a center point of an adjacent element 10. The base 20 and the plurality of elements 10 may be fabricated such that the elements 10 are equally spaced from each other. In another embodiment, the base 20 and the plurality of elements 10 may be fabricated such that the individual elements are unequally separated from each other along the base 20. In such an embodiment, the element density is an average of the measured distances between each element 10. In one embodiment, the base 20 has an element density from about 0.05 mm to about 5.0 mm, more particularly from about 0.1 mm to about 3.0 mm, or more particularly from about 0.1 to about 2 mm. Although the base 20 is shown in FIG. 1A as having a circular shape, it is understood that the base 20 may comprise other configurations, sizes, and shapes, including but not limited to polygon-shaped, elliptical-shaped, U-shaped, U-shaped forming a channel, and other configurations operable to insert into an oral cavity and enable the plurality of bristles to engage the oral cavity tissues therein.

FIG. 1A shows each element 10 having a transverse cross sectional area that remains constant from the proximal end 14 to the distal end 12. In another embodiment, each element 10 may taper inwardly toward the longitudinal axis A-A' from the proximal end 14 to the distal end 12. As such, the cross sectional area of the element 10 transverse to the longitudinal axis A-A' ("transverse cross sectional area") at the proximal end 14 is larger than the transverse cross sectional area at the distal end 12. Alternatively, each element 10 may taper outwardly away from the longitudinal axis A-A' from the proximal end 14 to the distal end 12. As such, the transverse cross sectional area of the element 10 at the proximal end 14 is smaller than the transverse cross sectional area at the distal end 12. In yet another embodiment, the oral care implement 1 may comprise a plurality of elements having constant transverse cross sections, inwardly tapering transverse cross sections, outwardly tapering transverse cross sections, or any combination thereof.

Figure 1B:
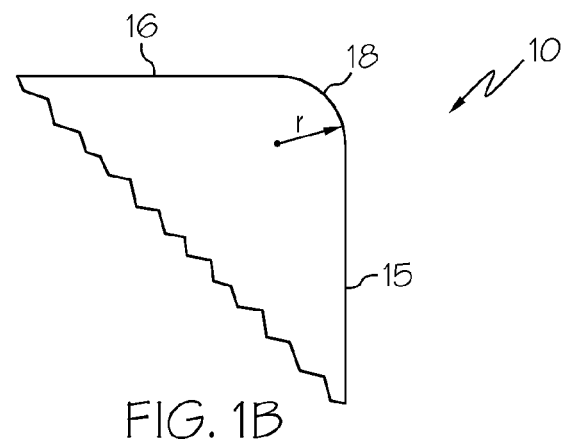
FIG. 1B is a detail of a top planar view of a flexible, elastomeric element of FIG. 1A.

As shown in FIG. 1A, the plurality of elements 10 have a round transverse cross sectional shape. As such, the elements 10 shown in FIG. 1A, only comprise one edge 18 that is transverse to the longitudinal axis A-A' ("transverse edge"). The edge 18 is disposed at the intersection of transverse surface 16 and side surface 15. FIG. 1B shows the edge 18 having a tip radius (r). In one embodiment, one or more of the plurality of elements 10 may be fabricated using the plastic injection method and mold system described below herein such that the edge 18 is a micro edge, wherein the micro edge has a tip radius (r) as defined above herein. Until the discovery of the method and mold system shown and described herein, it was not possible to injection mold plastic, such as an elastomeric material, into mold cavity corners sufficient enough to fabricate micro edges as defined herein.

In another embodiment, the edge 18 may comprise a tip radius (r) having any conventional value. In yet another embodiment, the edge 18 may comprise a tip radius as shown and described in U.S. Pat. Pub. No. 2009/0007357, and herein incorporated by reference.

Figure 2A:
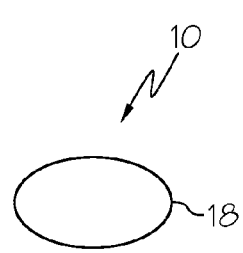
FIG. 2A is a top planar view of another embodiment of a flexible, elastomeric element.
Figure 2B:
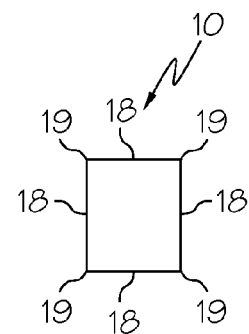
FIG. 2B is a top planar view of another embodiment of a flexible, elastomeric element.
Figure 2C:
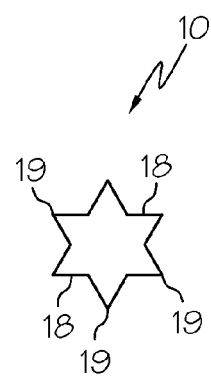
FIG. 2C is a top planar view of another embodiment of a flexible, elastomeric element.
Figure 2D:
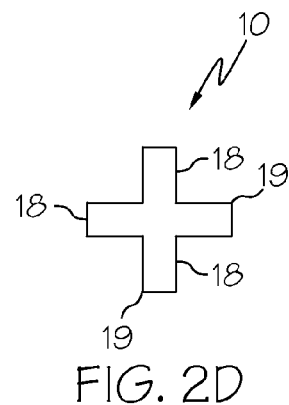
FIG. 2D is a top planar view of another embodiment of a flexible, elastomeric element.
Figure 2E:
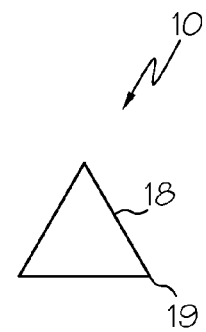
FIG. 2E is a top planar view of another embodiment of a flexible, elastomeric element.
Figure 3:
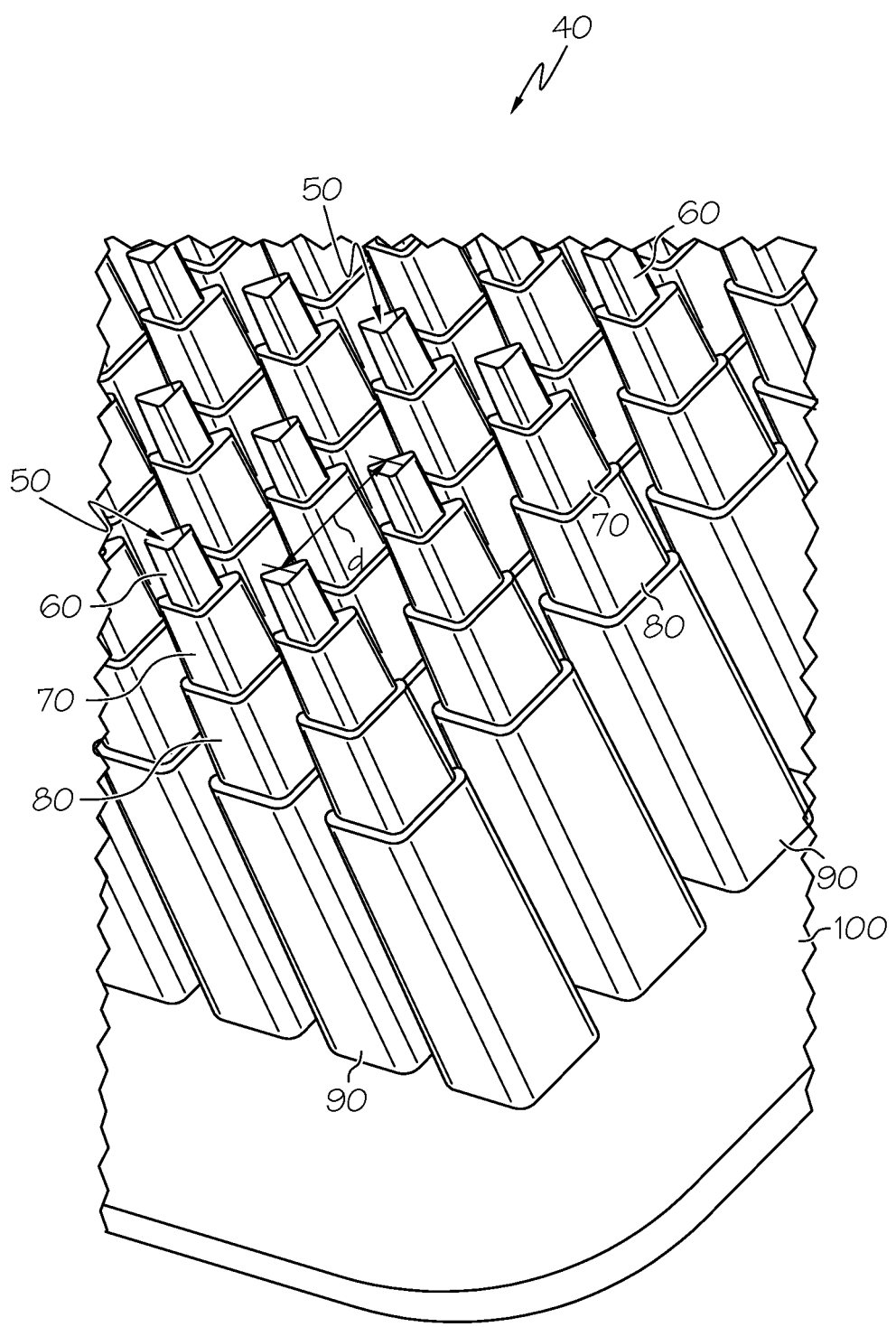
FIG. 3 is a partial perspective view of another embodiment of an oral care implement.

In other embodiments, the elements 10 may comprise a transverse cross-section having a variety shapes, sizes, and configurations, including but not limited to circular-shaped as shown in FIG. 1A, oval-shaped as shown in FIG. 2A, elliptical-shaped, polygonal-shaped (not shown), tetrahedron-shaped (not shown), square-shaped FIG. 2B, rectangle-shaped (FIG. 2B), star-shaped as shown in FIG. 2C, cross-shaped as shown in FIG. 2D, triangle-shaped as shown in FIG. 2E, sinusoidal-shaped (not shown), other conventional shaped configurations, and/or combinations thereof. In addition, the element 10 may have a single, continuous transverse cross sectional area and shape as shown, for example, in FIG. 1A. Alternatively, the element may include one or more segments, wherein each segment may have a different transverse cross sectional area and/or shape as shown, for example, in FIGS. 3 and 9. The shape of the transverse cross-section of the element may be determined based upon the number of edges and/or flat surfaces desired.

As shown in FIGS. 2B, 2C, 2D, and 2E, the element 10 may comprise one or more transverse edges 18 and one or more edges 19 that are disposed substantially along the longitudinal axis A-A' ("longitudinal axis"). In the alternative embodiments shown in FIGS. 2B, 2C, 2D, and 2E, the elements 10 may be fabricated such that one or more of the transverse edges 18, longitudinal edges 19, or a combination of the two may comprise a micro edge, wherein the micro edge has a tip radius (r) as defined above herein. Alternatively, in the embodiments shown in FIGS. 2B, 2C, 2D, and 2E, the elements 10 may be fabricated such that one or more of the transverse edges 18, longitudinal edges 19, or a combination of the two may comprise a conventional edge tip radius as shown and described in U.S. Pat. Pub. No. 2009/0007357, and herein incorporated by reference. Also, the embodiments shown in FIGS. 2B, 2C, 2D, and 2E, the elements 10 may be fabricated such that one or more of the transverse edges 18, longitudinal edges 19, or a combination of the two may include some mixture of both micro edges and conventional edges.

Referring to FIGS. 3-8, another embodiment of an oral care implement 40 is shown. The oral care implement 40 comprises a base 100 and a plurality of elements 50 extending from the base 100. The elements 50 comprise a proximal end 54 connected to the base 100 and a distal end 52 opposite the proximal end. As shown, the elements 50 may comprise four segments: a first segment 60 at the distal end 52; a second segment 70 disposed at an end of the first segment 60 opposite the distal end 52; a third segment 80 disposed at an end of the second segment 70 opposite the first segment; and a fourth segment 90 disposed at an end of the third segment 80 opposite the second segment. In is understood that the elements 50 may comprise any number of segment, including but not limited to one, two, three, or any other number. The segments may be fabricated such that the segments are integral to each other such as, for example integrally formed using a plastic injection molding process. In another embodiment, each segment may be fabricated as separate components that then are attached to adjacent segments using conventional connection techniques or devices, including but not limited to welding, adhesives, snap-fit connections, etc.

In the embodiment shown, the base 100 and the plurality of elements 50 are fabricated as one integrated unit to form, at least in part, the oral care implement 40. It is understood that the base 100 and the plurality of elements 50 may be two separate components that are connected together using conventional techniques and methods of connection such as, for example, adhesives, knotting, sonic welding, etc.

Figure 6:
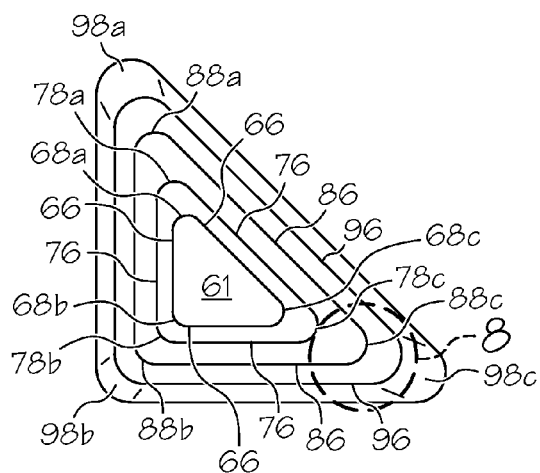
FIG. 6 is a top planar view of the flexible, elastomeric element of FIG. 4.

Referring particularly to FIGS. 4, 5, and 6, the elements 50 in this embodiment comprise a triangular-shaped transverse cross section. As such, the first segment 60 comprises a transverse surface 61, three longitudinal surfaces 63, a transverse edge 66, a first longitudinal edge 68a, second longitudinal edge 68b, and a third longitudinal edge 68c. Additionally, the second segment 70 comprises a transverse surface 71, three longitudinal surfaces 73, a transverse edge 76, a first longitudinal edge 78a, second longitudinal edge 78b, and a third longitudinal edge 78c. Also, the third segment 80 comprises a transverse surface 81, three longitudinal surfaces 83, a transverse edge 86, a first longitudinal edge 88a, second longitudinal edge 88b, and a third longitudinal edge 88c. Also, the fourth segment 90 comprises a transverse surface 91, three longitudinal surfaces 93, a transverse edge 96, a first longitudinal edge 98a, second longitudinal edge 98b, and a third longitudinal edge 98c.

Figure 7:
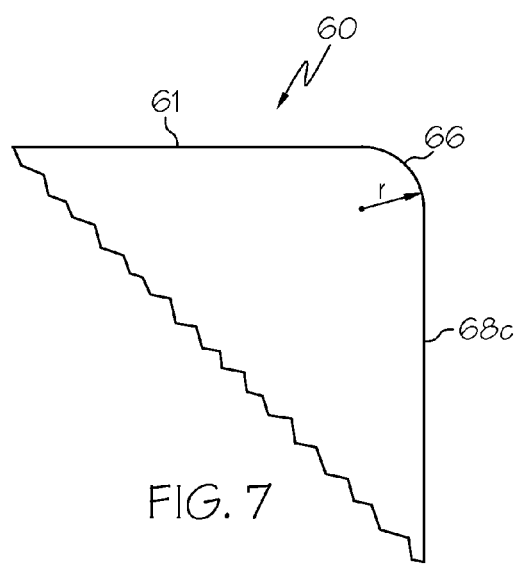
FIG. 7 is a detail of a top planar view of the flexible, elastomeric element of FIG. 5.

FIG. 7 shows the transverse edge 66 having a tip radius (r). The transverse edges 76, 86, and 96 may also comprise a tip radius as shown and measured in FIG. 7. In one embodiment, the element 50 may include one or more transverse edges 66, 76, 86, and/or 96 that comprise a micro edge as defined above herein. In another embodiment, the element 50 may include one or more transverse edges 66, 76, 86, and/or 96 that may comprise a conventional edge tip radius as shown and described in U.S. Pat. Pub. No. 2009/0007357, and herein incorporated by reference. It is understood that the oral care implement 40 may be fabricated such that none of the elements 50 comprise a micro, transverse edge or all the elements 50 have at least one micro, transverse edge.

Figure 8:
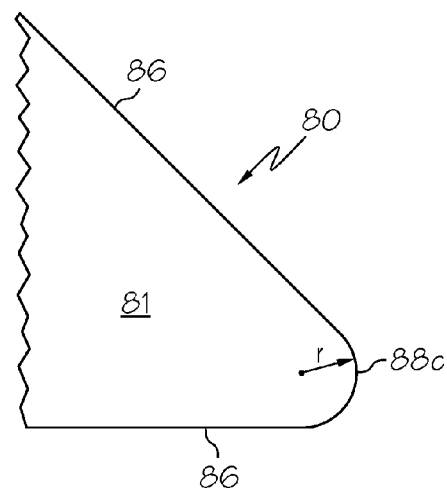
FIG. 8 is a detail of the flexible, elastomeric element of FIG. 6.

FIG. 8 shows the longitudinal edge 88c having a tip radius (r). The longitudinal edges 68a, 68b, 68c, 78a, 78b, 78c, 88a, 88b, 98a, 98b, and 98c may also comprise a tip radius (r) as shown and measured in FIG. 8. In one embodiment, the element 50 may comprise one or more longitudinal edges 68a, 68b, 68c, 78a, 78b, 78c, 88a, 88b, 88c, 98a, 98b, and/or 98c that comprise a micro edge as defined herein. In another embodiment, the element 50 may comprise one or more longitudinal edges 68a, 68b, 68c, 78a, 78b, 78c, 88a, 88b, 88c, 98a, 98b, and/or 98c that comprise a conventional edge tip radius as shown and described in U.S. Pat. Pub. No. 2009/0007357, and herein incorporated by reference. It is understood that the oral care implement 40 may be fabricated such that none of the elements 50 comprise a micro, longitudinal edge or all the elements 50 have at least one micro, longitudinal edge.

Referring back to FIG. 5, the element 50 comprises a length (L). Length (L) may comprise from about 0.05 mm to about 10 mm, particularly from about 0.1 mm to about 8 mm, more particularly from about 1.0 mm to about 7 mm, or more particularly from about 2.0 mm to about 6 mm. In one embodiment, the length (L) of the element 50 may comprise about 4 mm. Each of the first, second, third, and fourth segments 60, 70, 80 and 90 may comprise any length as desired. In addition, the first segment 60 may have a first segment width ($W_1$) from about 0.06 to about 1.0 mm, a segment width ($W_2$) from about 0.07 mm to about 2.0 mm, a third segment width ($W_3$) from about 0.09 mm to about 3.0 mm, and a fourth width ($W_4$) from 0.1 mm to about 4.0 mm.

One or more of the longitudinal surfaces 63, 73, 83, and 93 may be oriented at an angle α relative to an imaginary vertical plane (e.g., vertical plane M shown in FIG. 5). The angle α may less than about 30 degrees, particularly less than about 20 degrees, more particularly less than about 15 degrees, more particularly less than about 10 degrees, even more particularly less than about 5 degrees, and/or from about 0 degrees to about 90 degrees, from about 15 degrees to about 75 degrees, particularly from about 30 degrees to about 60 degrees, more particularly from about 0 degrees to about 45 degrees, even more particularly from about 0 degrees to about 30 degrees, even more particularly from about 0 degrees to about 15 degrees, even still more particularly from about 0 degrees to about 10 degrees, or even still more particularly about 1.5 degrees.

The oral care implement 40 may comprise an element density of the plurality of elements 50, which comprises the spacing between each adjacent element 50. As such, the element density may be measured by measuring the distance (d) between a center point of one element 50 to a center point of an adjacent element 50. The base 100 and the plurality of elements 50 may be fabricated such that the elements 50 are equally spaced from each other. In another embodiment, the base 100 and the plurality of elements 50 may be fabricated such that the individual elements are unequally separated from each other along the base 100. In such an embodiment, the element density is an average of the measured distances between each element 50. In one embodiment, the base 100 has an element density from 0.09 mm to about 0.4 mm, more particularly from about 0.1 mm to about 3.0 mm, or more particularly from about 0.2 mm to about 2 mm.

Figure 9:
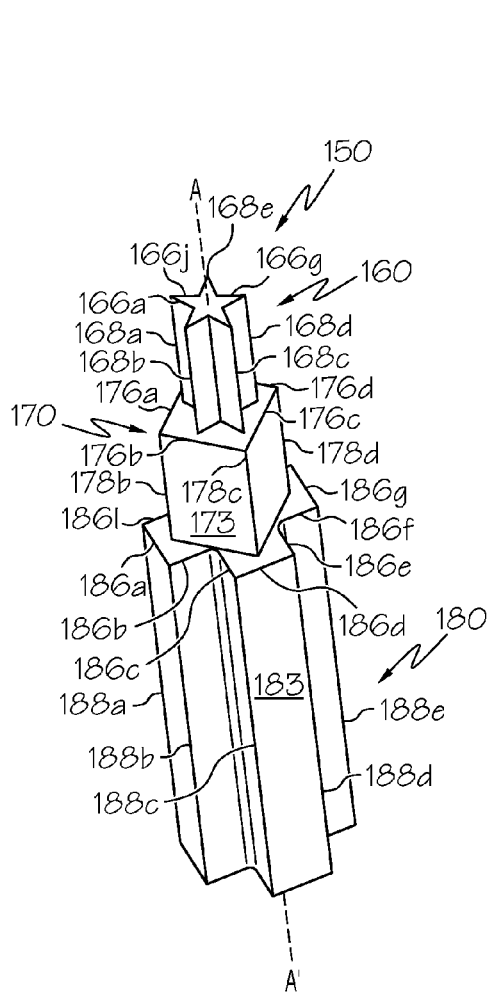
FIG. 9 is a perspective view of another embodiment of a flexible, elastomeric element.
Figure 10:
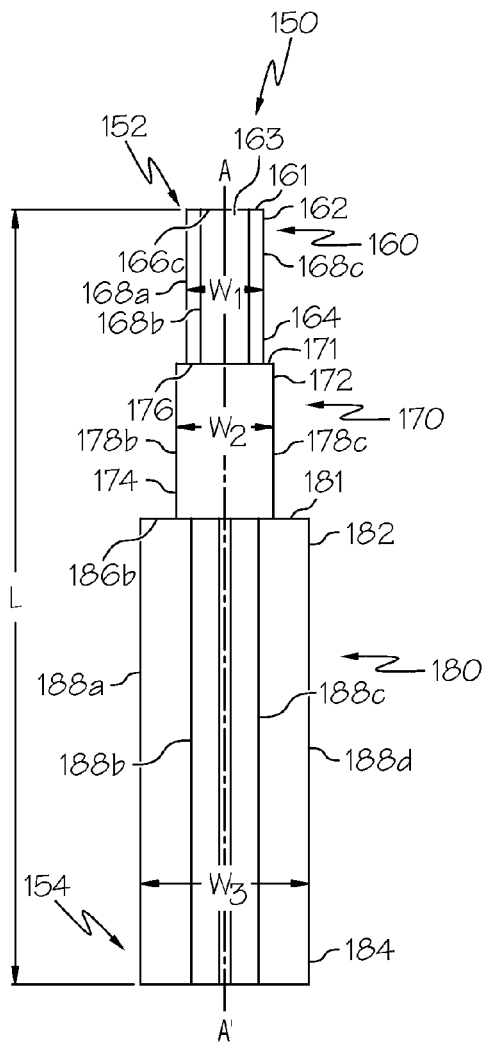
FIG. 10 is a side elevational view of the flexible, elastomeric element of FIG. 9.
Figure 11:
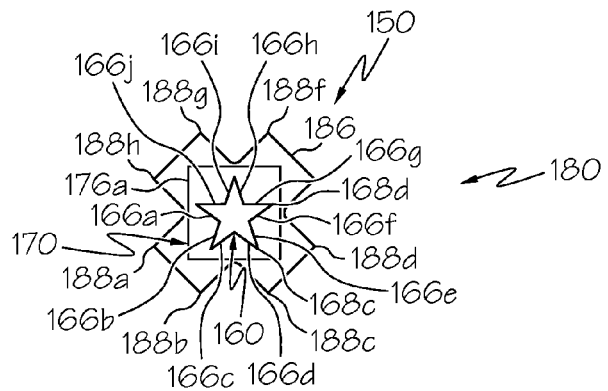
FIG. 11 is a top planar view of the flexible, elastomeric element of FIG. 9.

Referring to FIGS. 9-11, another embodiment of an element for an oral care implement (not shown but may be the same as or similar to those oral care implements shown and described herein, e.g., oral care implements 1, 40) is shown as 150. The element 150 may a proximal end 154 and a distal end 152 opposite of the proximal end 154. As in other embodiments shown and described herein, the element 150 may extend from a base (not shown), wherein the proximal end 154 is integral with or connected to the base. As also in the other embodiments, a plurality of elements 150 may extend from the base to form, in part, an oral care implement.

As shown, the element 150 may comprise three segments: a first segment 160 at the distal end 152; a second segment 170 disposed at an end of the first segment 160 opposite the distal end 152; a third segment 180 disposed at an end of the second segment 170 opposite the first segment 160. As set forth above with reference to the other embodiments, the element 150 may comprise any number of segment, each having any number of shapes, sizes, and configurations. As with the element's connection with the base, the segments (e.g., first, second, and third segment 160, 170, and 180) may be fabricated such that the segments are integral to each other such as, for example integrally formed using a plastic injection molding process. In another embodiment, each segment may be fabricated as separate components which then may be attached to adjacent segments using conventional connection techniques or methods, including but not limited to welding, adhesives, knotting, snap-fit connections, etc.

The first segment 160 may comprise a star-shaped transverse cross section as shown in FIGS. 9 and 11. The first segment 160 comprises a transverse surface 166, ten longitudinal surfaces 163, ten transverse edges 166a-j (traversing about the longitudinal axis A-A' of the first segment in a counter clockwise direction), and ten longitudinal edge 168a-j (traversing about the longitudinal axis A-A' of the first segment in a counter clockwise direction). The second segment 170 may comprise a square-shaped transverse cross section. The second segment 170 comprises a transverse surface 171, four longitudinal surfaces 173, four transverse edges 176a-d (traversing about the longitudinal axis A-A' of the second segment in a counter clockwise direction), and four longitudinal edges 178a-d. The third segment 180 may comprise a cross-shaped transverse cross section. The third segment 180 comprises a transverse surface 181, twelve longitudinal surfaces 183, twelve transverse edges 186a-l (traversing about the longitudinal axis A-A' of the third segment in a counter clockwise direction), and eight longitudinal edges 188a-h. The transverse edges 166a-j, 176a-d, and 186a-l and longitudinal edges 168a-e, 178a-d, and 188a-h of implement 150 may comprise a tip radius (r) such as, for example, the tip radius shown and measured in FIGS. 7 and 8.

In the embodiment shown in FIGS. 9-11, the first segment 160, second segment 170, and third segment 180, each have a transverse cross sectional area that is different from the other segments' transverse cross sectional area. Specifically, the first segment's transverse cross section area is smaller than the second and third segments' transverse cross sectional areas, and the second segment's transverse cross sectional area is smaller than the third segment's transverse cross sectional area, giving the element 150 a tiered configuration. It is also understood that the longitudinal edges of the first, second, and/or third segments may be oriented at any angle (e.g., angle α as shown in FIG. 5) relative to the longitudinal axis. The angle α may less than about 30 degrees, particularly less than about 20 degrees, more particularly less than about 15 degrees, more particularly less than about 10 degrees, even more particularly less than about 5 degrees, and/or from about 0 degrees to about 90 degrees, from about 15 degrees to about 75 degrees, particularly from about 30 degrees to about 60 degrees, more particularly from about 0 degrees to about 45 degrees, even more particularly from about 0 degrees to about 30 degrees, even more particularly from about 0 degrees to about 15 degrees, even still more particularly from about 0 degrees to about 10 degrees, or even still more particularly about 0 degrees.

Referring to FIG. 10, the element 150 comprises a length (L). Length (L) may comprise from about 0.5 mm to about 10 mm, particularly from about 1.0 mm to about 8 mm, more particularly from about 2.0 mm to about 7 mm, or more particularly from about 3.0 mm to about 6 mm. In one embodiment, the length (L) of the element 150 may comprise about 4 mm. Each of the first, second, and third segments 160, 170, and 180 may comprise any length as desired. In addition, the first segment 60 may have a first segment width ($W_1$) from about 0.06 mm to about 1.0 mm, a segment width ($W_2$) from about 0.07 mm to about 2.0 mm, and a third segment width ($W_3$) from about 0.09 mm to about 3.0 mm. The width as used herein may comprise the longest dimension along the transverse cross section. As with the length, the segments of element 150 may comprise any width as desired.

The oral care implement may comprise an implement density of the plurality of elements 150, which comprises the spacing between each adjacent element 150. As such, the element density may be measured by measuring the distance between a center point of one element 150 to a center point of an adjacent element 150. The base and the plurality of elements 150 may be fabricated such that the elements 150 are equally spaced from each other. In another embodiment, the base and the plurality of elements 150 may be fabricated such that the individual elements are unequally separated from each other along the base. In such an embodiment, the element density is an average of the measured distances between each element 150. In one embodiment, the base has an element density from 0.09 mm to about 0.4 mm, more particularly from about 0.1 mm to about 3.0 mm, or more particularly from about 0.2 mm to about 2 mm.

In one embodiment, one or more of the transverse edges (e.g., transverse edges 166a-j, 176a-d, and 186a-l of the element 150 may comprise a micro edge. In another embodiment, one or more of the longitudinal edges 168a-e, 178a-d, and 188a-h of element 150 may comprise a micro edge. In yet another embodiment, the element 150 may comprise the transverse edges 166a-j, 176a-d, and 186a-l and longitudinal edges 168a-e, 178a-d, and 188a-h, wherein at least one of the traverse edges and at least one of the longitudinal edges are micro edges, edges, or combinations thereof.

An oral care implement (e.g., oral care implement 1 of FIG. 1) may comprise a plurality of element such as, for example, element 150, or a combination of elements such as, for example, elements 50, or other conventional or yet-to-be developed elements. The several examples of the elements (e.g., 10, 50, 150, 2050) and bases (e.g., 20, 100, 2100) shown and described herein may be fabricated from a variety of materials, particularly materials used for oral care applications such as, for example materials used for oral care bristles, flexible elements, etc. In one embodiment, the elements (e.g., 10, 50, 150, 2050) are fabricated from a compliant material for enhanced cleaning with reduced abrasion. The bases (e.g., 20, 100, 2100) may be fabricated from the same or different material as the elements depending upon the properties desired. Also, the material used for the fabrication of the elements and/or the bases may be a single substrate material, composite material, multi-laminate structure, or any combination thereof.

In one or more of the embodiments shown and described herein, the material used for the elements (e.g., 10, 50, 150, 2050) and/or bases (e.g., 20, 100, 2100) may comprise a flexible (or compliant) material, including but not limited to thermoplastic elastomers, rubber, flexible composites, and combinations thereof. In an embodiment, one or more of the plurality of elements (e.g., 10, 50, 150, 2050) and/or bases (e.g., 20, 100, 2100) may be formed of a thermoplastic or a cross-linked material (a thermoset material).

Examples of suitable elastomeric materials include one or more styrenic copolymers, thermoplastic polyurethanes, silicones, polyether-amides, polyether-polyesters, or mixtures of these and other elastomers. Any elastomeric material described herein can include one or more fillers. For example, the filler may be or may include oil, e.g., mineral oils, abrasives, tackifiers, plasticizers or mixtures of these and even others. As an example, the material that may be used for one or more of the plurality of element (e.g., 10, 50, 150, 2050) and/or bases (e.g., 20, 100, 2100) may comprise a flexible material having a Shore Hardness of from about 8 Shore A to about 75 Shore D, as a further example, from about 35 Shore A to about 55 Shore D.

Not to be limited by theory, the material hardness is believed to be highly correlated with and may be used to specify the desired stiffness/flexibility of the cleaning element(s) in order to manipulate how the cleaning element(s) will move (e.g., twisting, bending, and/or other deformation) and how significant this motion will be due to a driving motion provided to the oral care implement. Elastomeric materials enable the element(s) (e.g., elements 10, 50, 150, 2050) to twist, bend and otherwise deform, providing the element's cleaning edges (e.g., transverse and longitudinal edges) access to the plaque and debris at the various locations on surfaces of the teeth, including the interdental areas. (See, for example, FIGS. 24A-F). As set forth herein, the material used for the elements may be flexible enough to twist, bend, and deform in order to permit one or more elements to contact the teeth. However, in certain embodiments, if the element is too flexible, it will lack the rigidity, particularly its edges, to effectively, if at all, remove plaque and debris from the oral cavity surfaces. Thus, in some embodiments, the hardness of the material may also be configured in order that the stiffness/flexibility of the element(s) is sufficient and/or adequate enough that the cleaning edge (e.g., transverse and/or longitudinal edges) of the element is able overcome the plaque or debris' adhesion to the tooth's surface. Thus, some of the embodiments shown and described herein provide such a balance between the two competing factors.

In one embodiment, the material may comprise a thermoplastic elastomer, including but not limited to Pellethane 2363, which is commercially available from Dow Chemical Company, 4520 Ashman Street, Midland, Mich. 48642. In another embodiment, the compliant and/or flexible material used for the elements and/or base may have the following material properties: a hardness (durometer) from about 55 Shore A to about 55 Shore D; wet friction greater than about 0.05, particularly greater than about 0.1, more particularly greater than or equal to about 0.5 in order to create friction in the wet oral environment that may be sufficient enough such that the element edges engage the adhesion boundary between the plaque and the surface of the tooth, rather than slide over the surface of the plaque; surface pressure (contact angle) greater than about 500 $Nm^{-1}10^4$, more particularly greater than about 600 $Nm^{-1}10^4$, even more particularly greater than about 700 $Nm^{-1}10^4$, even more particularly about 727 $Nm^{-1}10^4$; and density from about 0.05 $g/cm^3$ to about 3.0 $g/cm^3$, from about 0.5 $g/cm^3$ to about 2.0 $g/cm^3$, more particularly 0.9 $g/cm^3$ to about 1.2 $g/cm^3$. One or more of the embodiments of the cleaning implement and its plurality of elements shown and described herein are configured such that the dislodged plaque and debris can be transported from the cleaning site with the aid of surface wetting and/or capillary action of the saliva, water and/or dentifrice/plaque/debris suspension or slurry.

In one embodiment, the elements (e.g., element 10, 50, 150, 2050, etc.) and base (e.g., bases 100, 200, etc.) are injection molded as one integral part with a hydraulic, screw injector, heated barrel, single cavity, water cooled mold, 55 ton conventional press machine as known to one of ordinary skill in the art. The part is molded with a single shot cycle. However, the process can be adapted to mold more than one part per cycle with a larger press and multiple cavities.

The plurality of elements (e.g., elements 10, 50, 150) and the base (e.g., bases 20, 100) may be fabricated using a molding process, particularly a plastic molding process, including but not limited to plastic injection molding, solution casting, micro-injection molding, or any other conventional or yet-to-be developed methods that do not impart polymer chain alignment as does a plastic extrusion process and thus found in extruded elastomeric elements. Injection molded elements are less directional, permitting more deformation in various cleaning motions and thus providing more degrees of freedom to the cleaning elements and providing greater access of the cleaning element's edges to the plaque along the surfaces of the teeth, including interdental areas. As set forth above, the plurality of elements and bases may be fabricated at two separate components using two separate molding processes, or they may be fabricated using one molding process to form a single, integral unit. In another embodiment, the plurality of elements (e.g., 10, 50, 150, 2050) and/or bases (e.g., 20, 100, 2100) may not comprise an extruded material, particularly extruded nylon, but consist of or only comprise elastomeric material that has been plastic injection molded to form such elements and/or bases. The nylon and extrusion process will not permit the material (e.g., nylon to flow deep enough into the corners of the mold cavity to form micro edges as defined herein).

Figure 12:
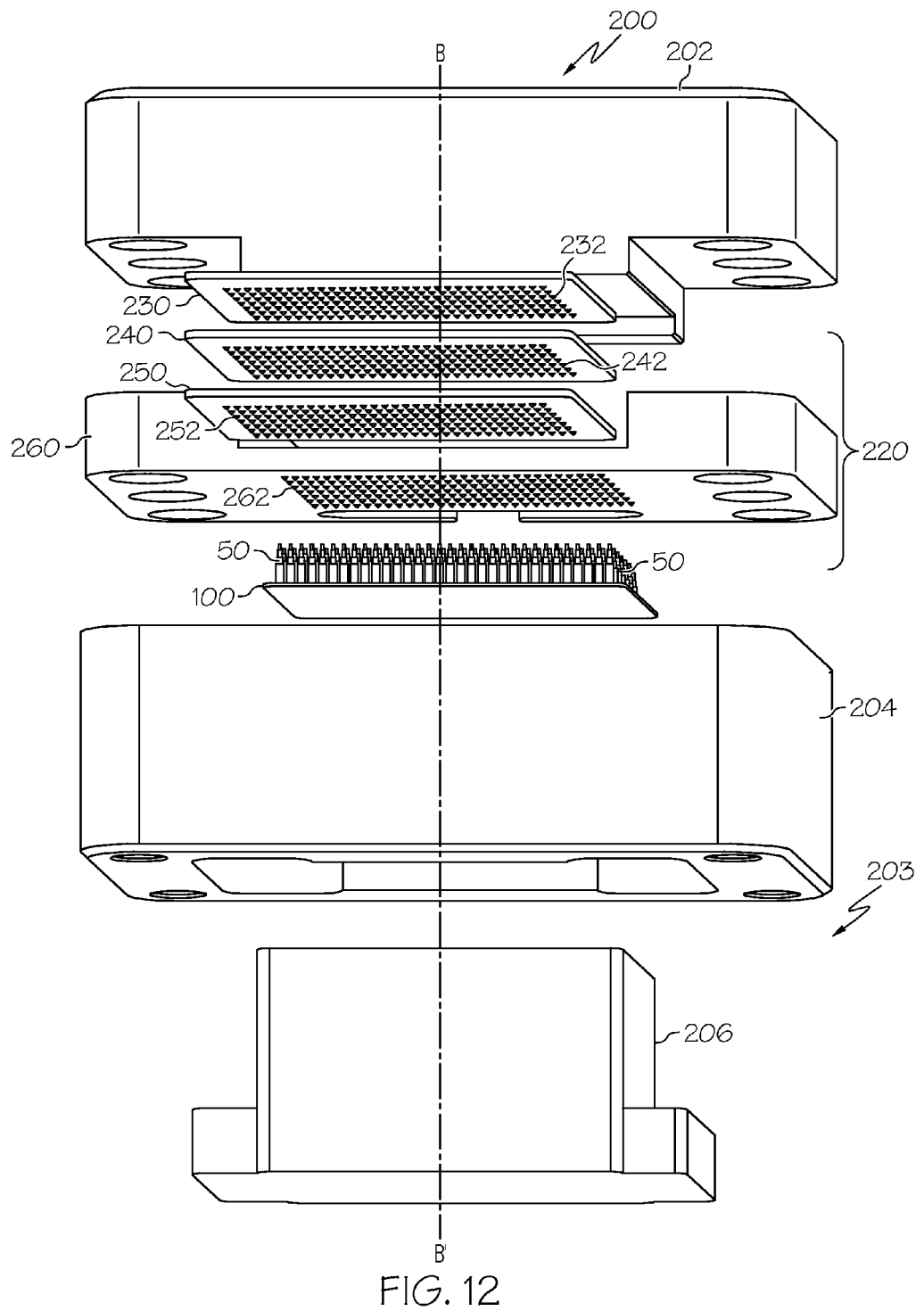
FIG. 12 is an exploded, perspective view of an embodiment of a mold system in combination with a mold machine.
Figure 13:
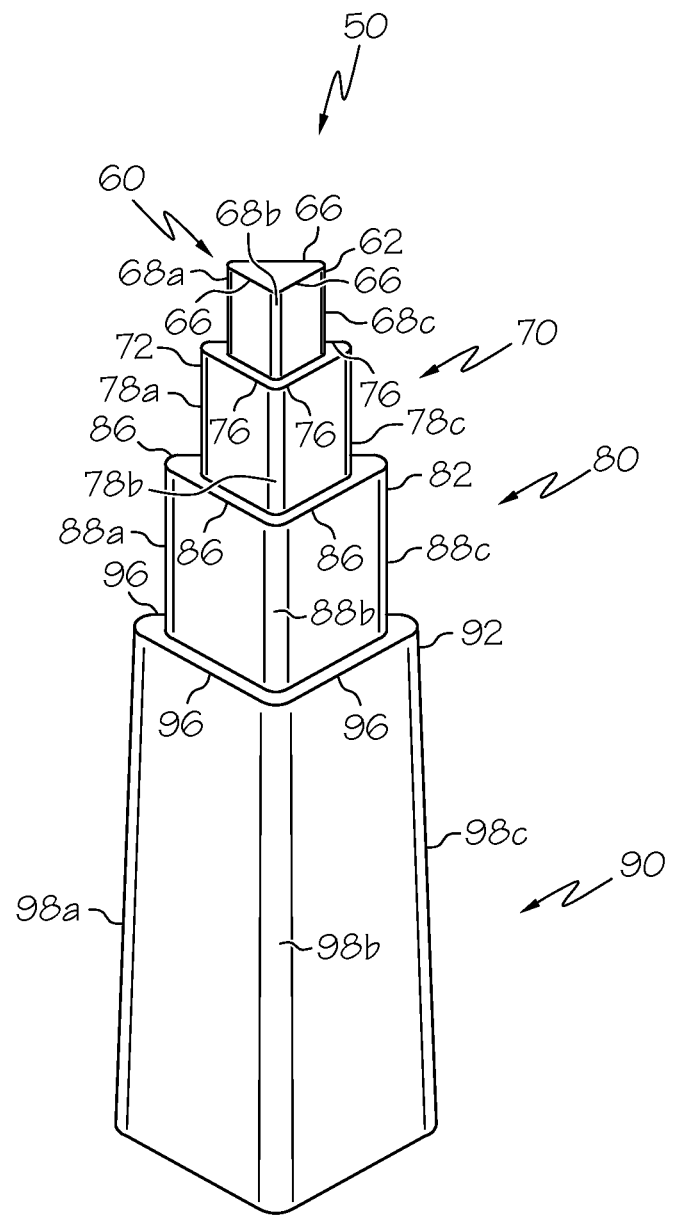
FIG. 13 is a perspective view of another embodiment of a flexible, elastomeric element fabricated from the mold system of FIG. 12.
Figure 14:
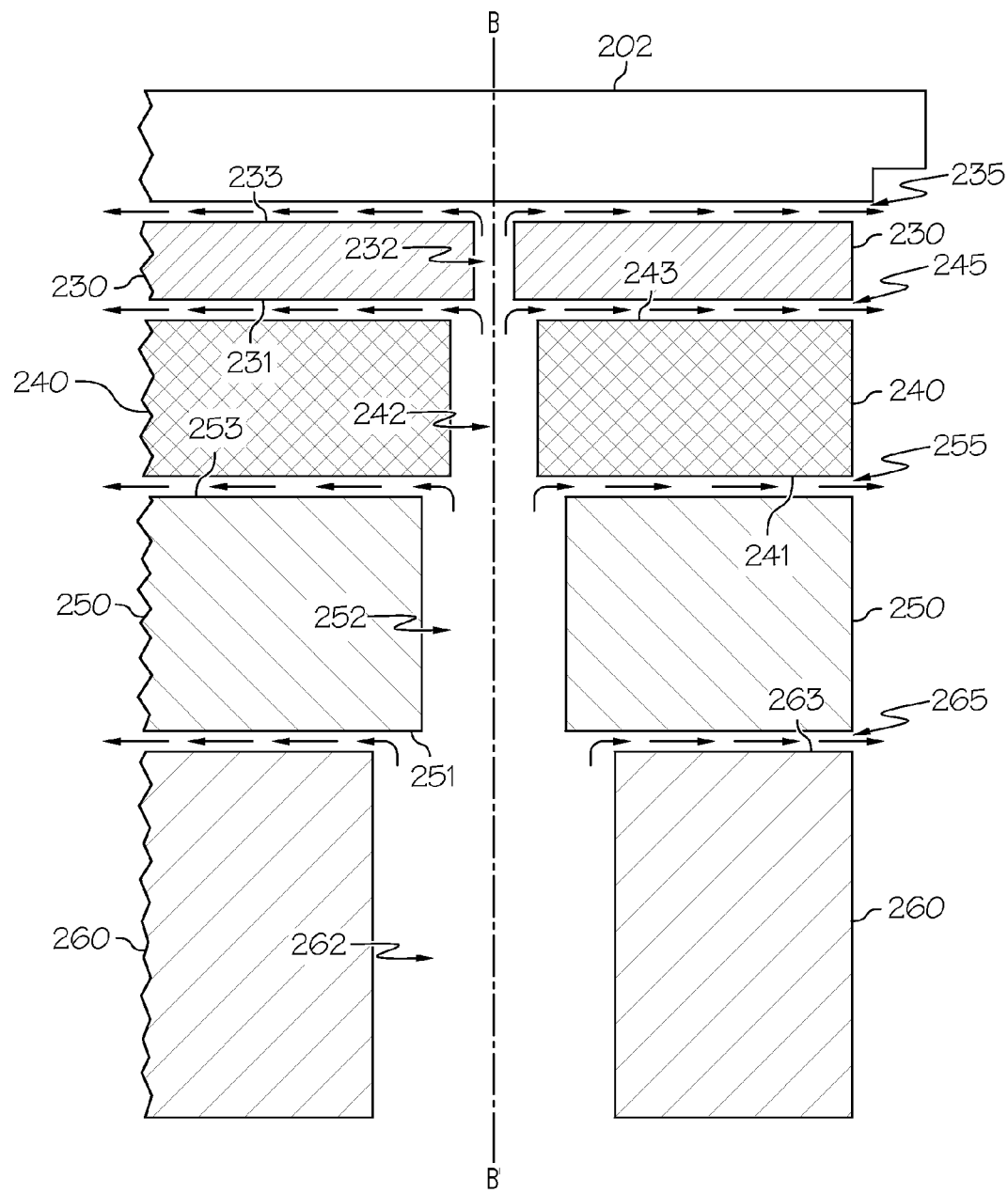
FIG. 14 is a partial cross sectional view of the mold system of FIG. 12.

Referring to FIGS. 12-14, an embodiment of a plastic injection mold system 220 is shown for illustration purposes only, and not limitation, in conjunction with a plastic injection mold machine 200 for molding one or more elements 50 and/or a base (e.g., base 100). The plastic injection mold system 220 may comprise one or more cavity mold plates. In one embodiment, the plastic injection mold system 220 comprises a first cavity mold plate 230, a second cavity mold plate 240, a third cavity mold plate 250, and a fourth cavity mold plate 260. The first, second, third, and fourth cavity mold plates 230, 240, 250, and 260 each comprise a plurality of mold cavities 232, 242, 252, and 262, respectively, disposed therein for forming the respective first, second, third, and fourth segments 60, 70, 80, and 90, respectively, of the plurality of elements 50. In other words, when the four cavity mold plates (e.g., 230, 240, 250, 260) are assembled together their respective mold cavities (e.g., 232, 242, 252, 262) form the mold cavities for molding the plurality of elements 50 having segments (e.g., segments 60, 70, 80, 90) corresponding to respective mold cavities (e.g., mold cavities 232, 242, 252, 262, respectively).

As shown, since the desired transverse cross sectional shape of each of the segments of the element 50 are triangular-shaped, the respective mold cavities are each triangular-shaped. The plurality of mold cavities 232, 242, 252, and 162 comprise the interior volume necessary to form the respective segments (e.g., segments 60, 70, 80, 90) to their desired size. The mold system 220, i.e., the assembled four cavity mold plates 230, 240, 250, and 260, is configured to be positioned within and connected to the conventional plastic injection mold machine 200. In this embodiment, the plastic injection mold machine 200 may comprise any variety of conventional plastic injection mold machines that are commercially available. The plastic injection mold machine 200 may comprise a cavity side mold plate 202 and a core side mold plate 203. The core side mold plate 203 may comprise an outer core module 204 and an inner core module 206.

As shown in FIG. 12, the first cavity mold plate 230 has first and second plate surfaces 231 and 233, respectively. Similarly, the second cavity mold plate 240 has first and second plate surfaces 241 and 243, respectively, and the third cavity mold plate 250 has first and second plate surfaces 251 and 253, respectively. The fourth cavity mold plate may include a first plate surface 263. When the cavity mold plates are assembled together in an transverse abutting configuration as shown in FIGS. 12 and 14, each pair of abutting, transverse mold cavity plates form a transverse intersection. For example, when the first plate surface 231 of first mold cavity plate 230 is abutted against the second plate surface 243 of the second mold cavity plate 240, a second transverse intersection 245 is formed as shown in FIG. 14. Similarly, FIG. 14 shows a third transverse intersection 255 is formed at the abutment of the first plate surface 241 of the second mold cavity plate 240 with the second plate surface 253 of the third mold cavity plate 250, and a fourth transverse intersection 265 is formed at the abutment of the first plate surface 251 of the third mold cavity plate 250 with the second plate surface 263 of the fourth cavity mold plate 260. Additionally, a first transverse intersection 235 may be formed between or at the abutment of the second plate surface 233 with a surface of the cavity side mold plate 202 (FIG. 14).

Not to be limited by theory, it is believed that as the plastic is injected into the plurality of mold cavities (e.g., the plurality of assembled mold cavities 232, 242, 252, and 262) during a plastic injection molding process, the gas contained within the mold cavities is forced or caused to exit and/or out-gas from the mold cavities through the spaces between the mold cavity plates 230, 240, 250, and 260, i.e., at the transverse intersections 235, 245, 255, and 265 between the mold cavity plates. The spaces between the mold cavity plates 230, 240, 250, and 260 at the respective transverse intersections shown in FIG. 14 are exaggerated for clarity purposes and not meant to be to scale or for limitation.

As shown in FIG. 14 and set forth above, the gas may exit and/or out-gas at the transverse intersections 235, 245, 255, and 265. Again, not to be limited by theory, it is believed that when the gas exits and/or out-gases from the mold cavities at and along these transverse intersections between the mold cavity plates, the gas pushes and/or draws the plastic deep into the respective corners of the mold cavity formed by these transverse intersections 235, 245, 255, and 265. In so doing, the plastic injection molding process is able to form micro edges at and along any intersection between two molding plates. As shown in FIGS. 13 and 14, the mold system 220 forms transverse edges 66, 76, 86, and 96 as micro edges at the respective transverse intersections 235, 245, 255, and 265. Such micro edges as shown and defined herein cannot be formed using known plastic extrusion processes as used to form conventional bristles and flexible elements, particularly bristles and flexible elements used in oral care devices.

Moreover, as set forth above, the conventional plastic injection mold processes and mold systems, including but not limited to those shown and described within U.S. Pat. Pub. No. 2009/0007357, cannot form and/or fabricate the micro edges as shown and defined herein. Although U.S. Pat. Pub. No. 2009/0007357 describes its plastic injection mold process and mold systems as forming sharp edges on flexible elements, it has been unexpectedly found that the mold system fabricates micro edges shown and described herein that include a tip radius that is a whole order of magnitude smaller than the tip radii of the sharp edges shown and described in U.S. Pat. Pub. No. 2009/0007357.

Figure 15A:
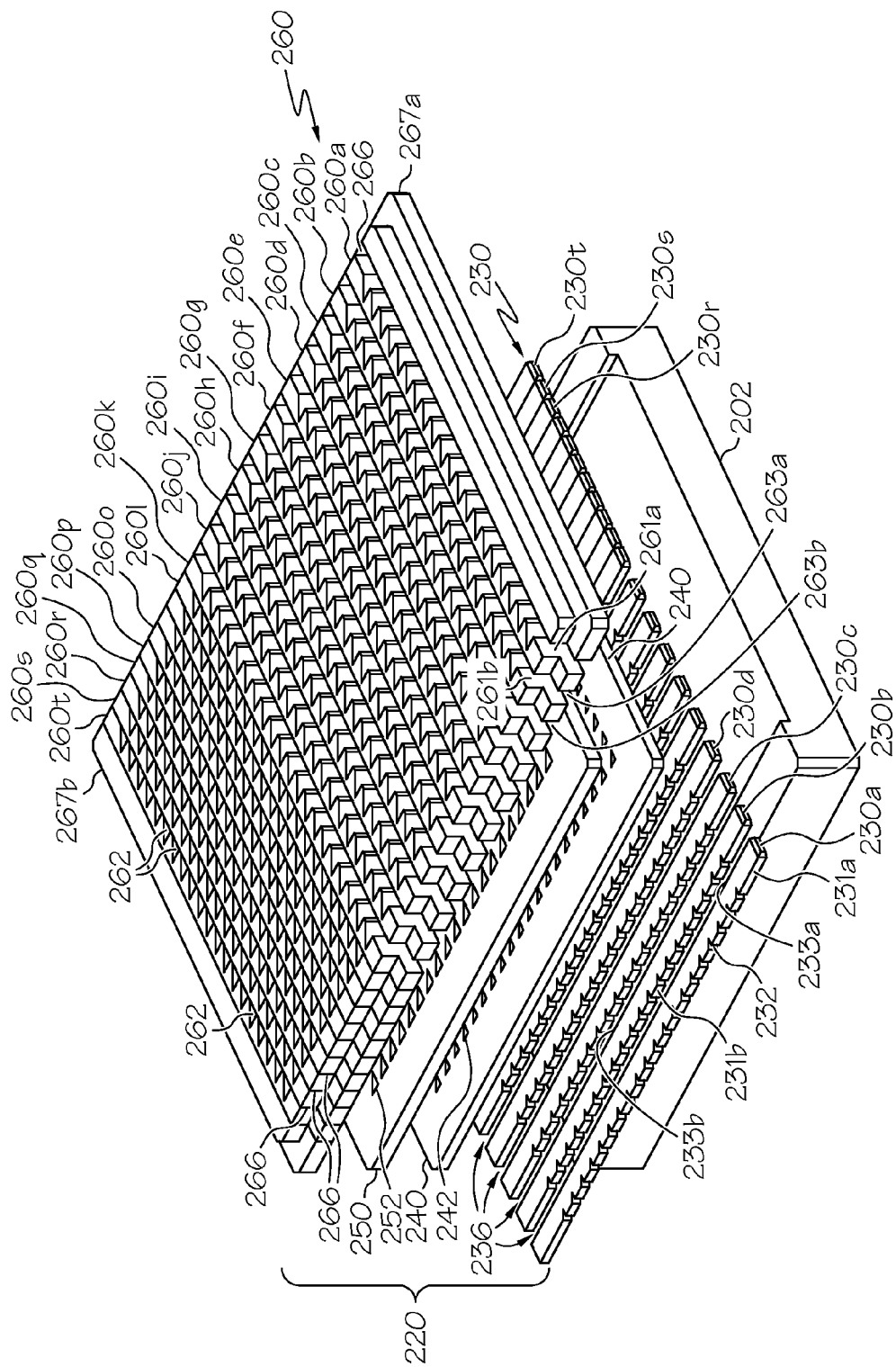
FIG. 15A is a an exploded, perspective view of another embodiment of a mold system.
Figure 15B:
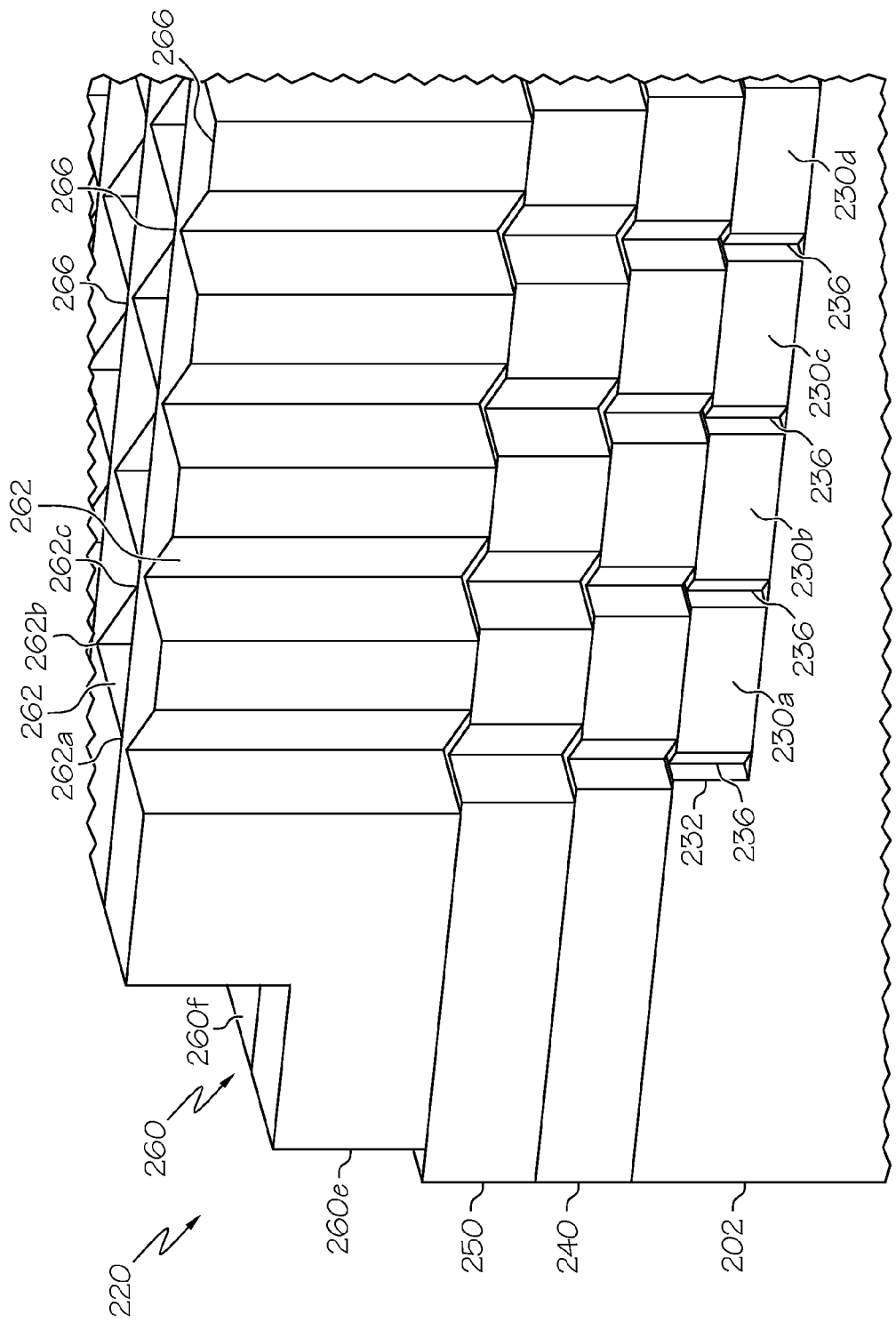
FIG. 15B is a partial perspective view of the mold system of FIG. 15A.
Figure 16:
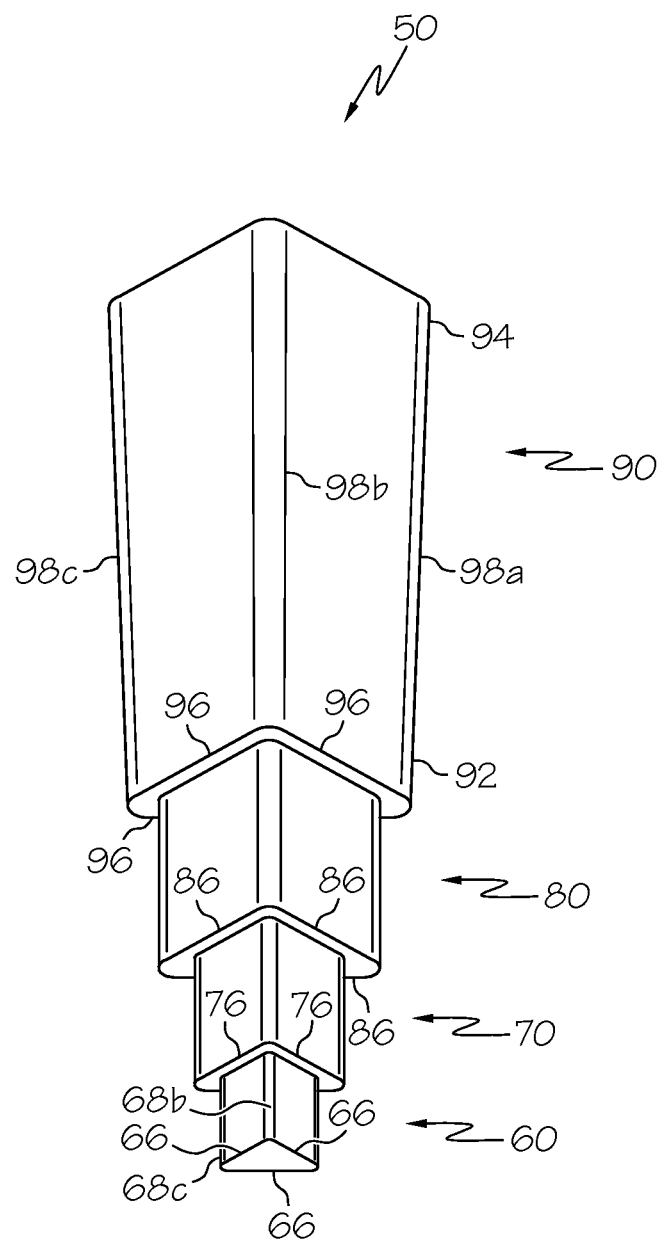
FIG. 16 is a perspective view of another embodiment of a flexible, elastomeric element fabricated from the mold system of FIG. 15A.

In order to form micro edges along the longitudinal edges 68a-c, 78a-c, 88a-c, and/or 98a-c, one or more of the cavity mold plates 230, 240, 250, 260 may be divided up into a plurality of longitudinal cavity mold plates, wherein each one may form a row of mold cavities or individual mold cavities as will be shown and described below with reference to the embodiments. Referring to FIGS. 15 and 16, another embodiment of a plastic injection mold system 220 is shown. The plastic injection mold system 220 comprises a first cavity mold plate 230, a second cavity mold plate 240, a third cavity mold plate 250, and a fourth cavity mold plate 260. In this embodiment, the first cavity mold plate 230 may comprise a plurality of longitudinal cavity mold plates 230a-230t, wherein each longitudinal cavity mold plate 230a-t comprises two longitudinal plate surfaces such as, for example, a first longitudinal plate surface 231a and a second longitudinal plate surface 233a of first longitudinal cavity mold plate 230a and a first longitudinal plate surface 231b and a second longitudinal plate surface 233b of second longitudinal cavity mold plate 230b. When the second longitudinal plate surface 233a abuts the first longitudinal plate surface 231b as shown in FIG. 15A, this intersection forms a longitudinal intersection 236. (See also FIG. 15B). Each consecutive longitudinal mold plate has similar first and second longitudinal plate surfaces forming their respective longitudinal intersections 236 as shown and described for the first longitudinal cavity mold plate 230a. In addition, each longitudinal cavity mold plate 230a-t forms a row of mold cavities to mold the first segments 60 of the plurality of elements 50.

The fourth cavity mold plate 260 also comprises a plurality of longitudinal cavity mold plates 260a-t, wherein each longitudinal cavity mold plate 260a-t comprises two longitudinal plate surfaces such as, for example, a first longitudinal plate surface 261a and a second longitudinal plate surface (263a) of first longitudinal cavity mold plate 260a and a first longitudinal plate surface 261b and a second longitudinal plate surface (263b) of second longitudinal plate surface 260b. When the second longitudinal plate surface 263a abuts the first longitudinal plate surface 261b as shown in FIGS. 15A and 15B, this intersection forms a longitudinal intersection 266. Each consecutive longitudinal mold plate has similar first and second longitudinal plate surfaces forming their respective longitudinal intersections 266 as shown and described for the first longitudinal cavity mold plate 260a. Also, a first and second longitudinal end mold plates 267a and 267b which form respective longitudinal intersections 266 with longitudinal cavity mold plate 260a and 260t, respectively, as shown in FIG. 15A. In addition, each longitudinal cavity mold plate 260a-t forms a row of mold cavities 262 to mold the fourth segments 90 of the plurality of elements 50. In this embodiment, the second and third cavity mold plates 240 and 250 are each a single mold plate comprising a plurality of mold cavities 242 and 252, respectively, therein to mold the second and third segments 70 and 80, respectively.

The first longitudinal cavity mold plates 230a-t, second cavity mold plate 240, third cavity mold plate, and fourth longitudinal cavity mold plates 260a-t may be assembled together and positioned within a conventional plastic injection mold machine (e.g., plastic injection mold machine 200 shown in FIG. 12). When assembled together, the first longitudinal cavity mold plates 230a-t, second cavity mold plate 240, third cavity mold plate, and fourth longitudinal cavity mold plates 260a-t form respective transverse intersections. For example, the first longitudinal cavity mold plates 230a-t as an assembly form a first transverse intersection 235 between the cavity side mold plate 202 and the plates 230a-t themselves. At the abutment of the first longitudinal cavity mold plates 230a-t with the second cavity mold plate 240, a second transverse intersection 245 is formed. The abutment of the second cavity mold plate 240 and the third cavity mold plate 250 forms a third transverse intersection 255. Also, the abutment of the third cavity mold plate 250 with the fourth cavity mold plates 260a-t forms a fourth transverse intersection 265. Once the cavity mold plates 230a-t, 240, 250, and 260 are assembled together to form the mold system 220, the mold system 220 may be disposed within and connected to a conventional plastic injection mold machine (e.g., similar to or the same as mold machine 200 shown in FIG. 12). Although not shown, mold machine will comprise a cavity side mold plate (e.g., cavity side mold plate 202 in FIG. 12) having a first surface.

Not to be limited by theory, it is believed that as the plastic is injected into the plurality of mold cavities (e.g., the plurality of assembled mold cavities 232, 242, 252, and 262), the gas contained within the mold cavities is forced or caused to exit and/or out-gas from the mold cavities between the cavity mold plates 230a-t, 240, 250, and/or 260a-t at and along any intersection between the mold plates (i.e., through the spaces between these plates) such as, for example, longitudinal intersections 236 and 266 and/or transverse intersections 235, 245, 255, and 265. Again, not to be limited by theory, when the gas exits and/or out-gases from the mold cavities at and along the transverse and/or longitudinal intersections, the gas pushes and/or draws the plastic deep into the corners of the mold cavities (e.g., mold cavity corners 262a and 262c shown in FIG. 15B). In so doing, the plastic injection molding process is able to form micro edges at and along any intersection, both transverse and longitudinal, between any two molding plates and/or between any mold plate and the cavity side mold plate 202.

Still referring to FIGS. 15 and 16, the mold system 220 forms transverse edges 66, 76, 86, and 96 of the plurality of elements 50 as micro edges using the respective transverse intersections 235, 245, 255, 265. In addition, the mold system 220 forms longitudinal edges 68b, 68c, 98a, and 98c of the plurality of elements 50 as micro edges using the respective longitudinal intersections 236 and 266 between the respective longitudinal cavity mold plates 230a-t and 260a-t. In this embodiment, micro edges (e.g., transverse and/or longitudinal micro edges) cannot be formed using a plastic extrusion process as used to form conventional bristles and flexible elements, particularly those used for oral care devices.

As set forth above, this mold system 220 may be inserted into and connected to a conventional plastic injection molding machine. As configured in this mold system 220. It is understood that if additional longitudinal edges were desired, both the second and third cavity mold plates 240 and 250 may also be divided up into longitudinal cavity mold plates as found and shown with the first and fourth cavity mold plates 230a-t and 260a-t, respectively.

Figure 17:
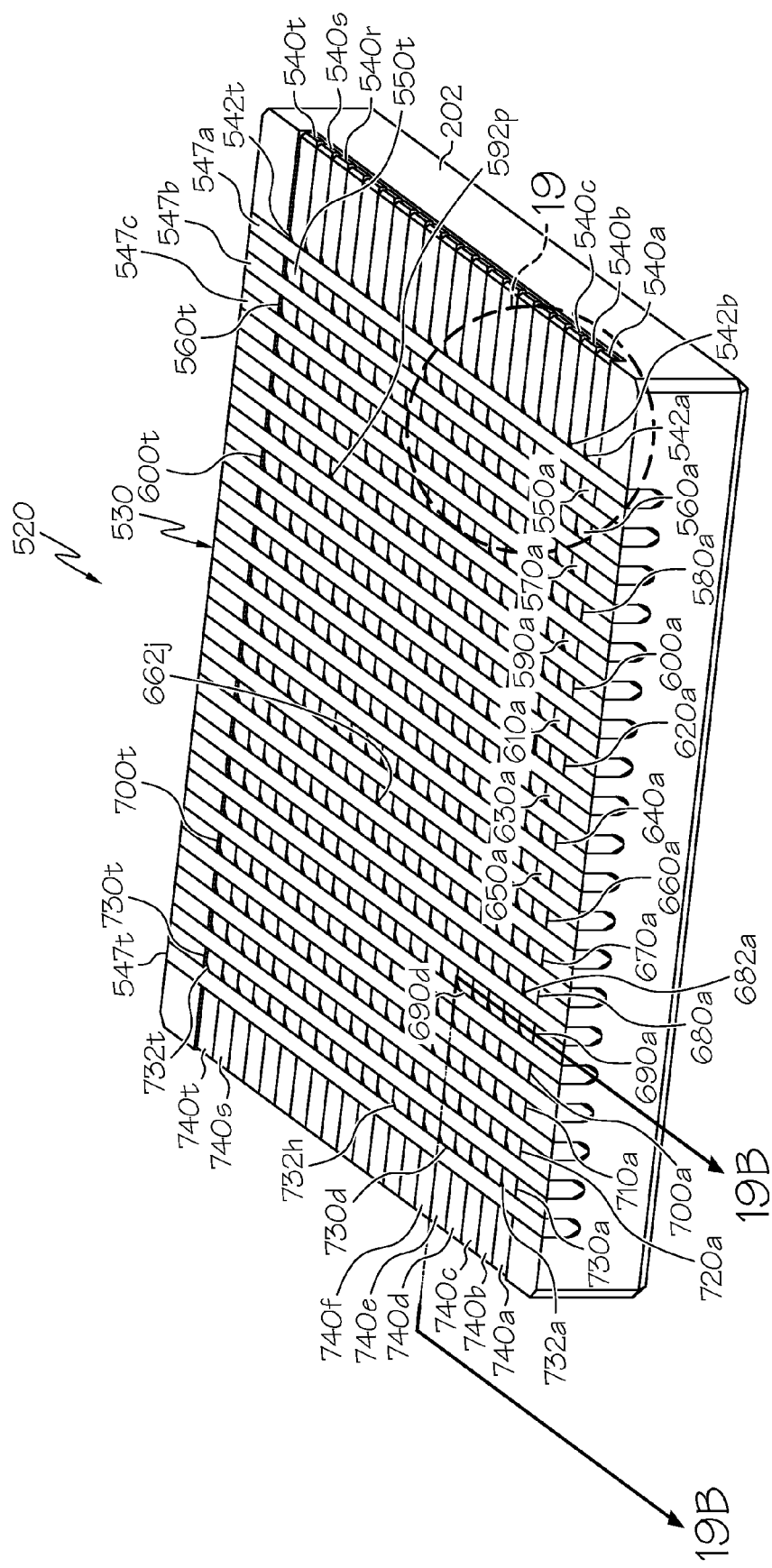
FIG. 17 is a perspective view of another embodiment of a mold system.
Figure 18:
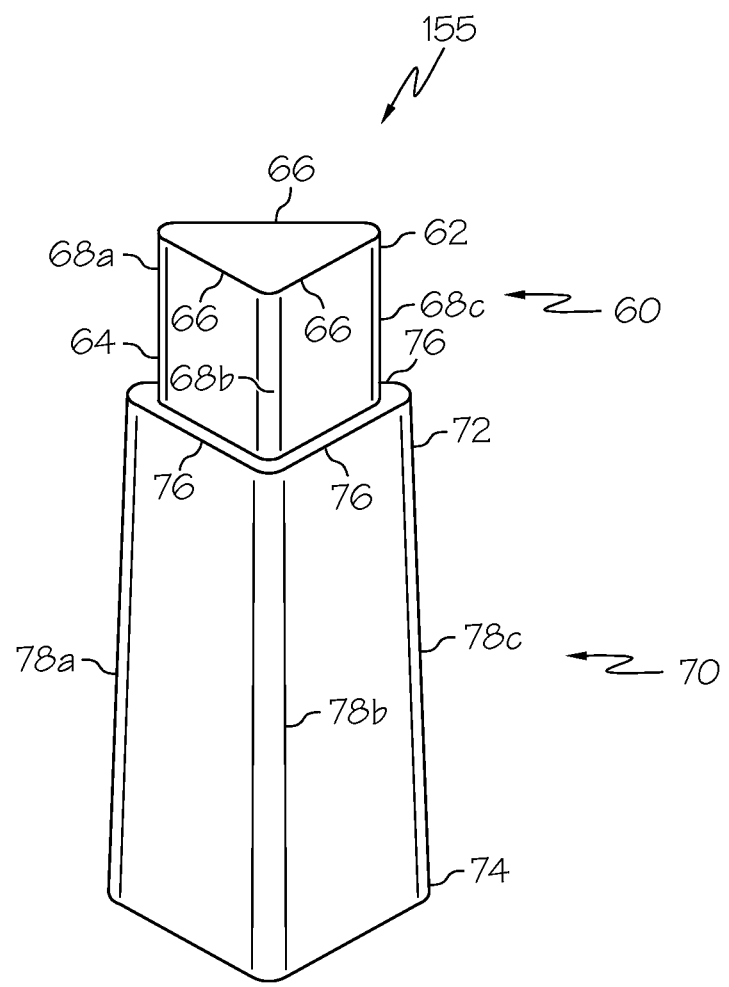
FIG. 18 is a perspective view of another embodiment of a flexible, elastomeric element fabricated from the mold system of FIG. 17.
Figure 19A:
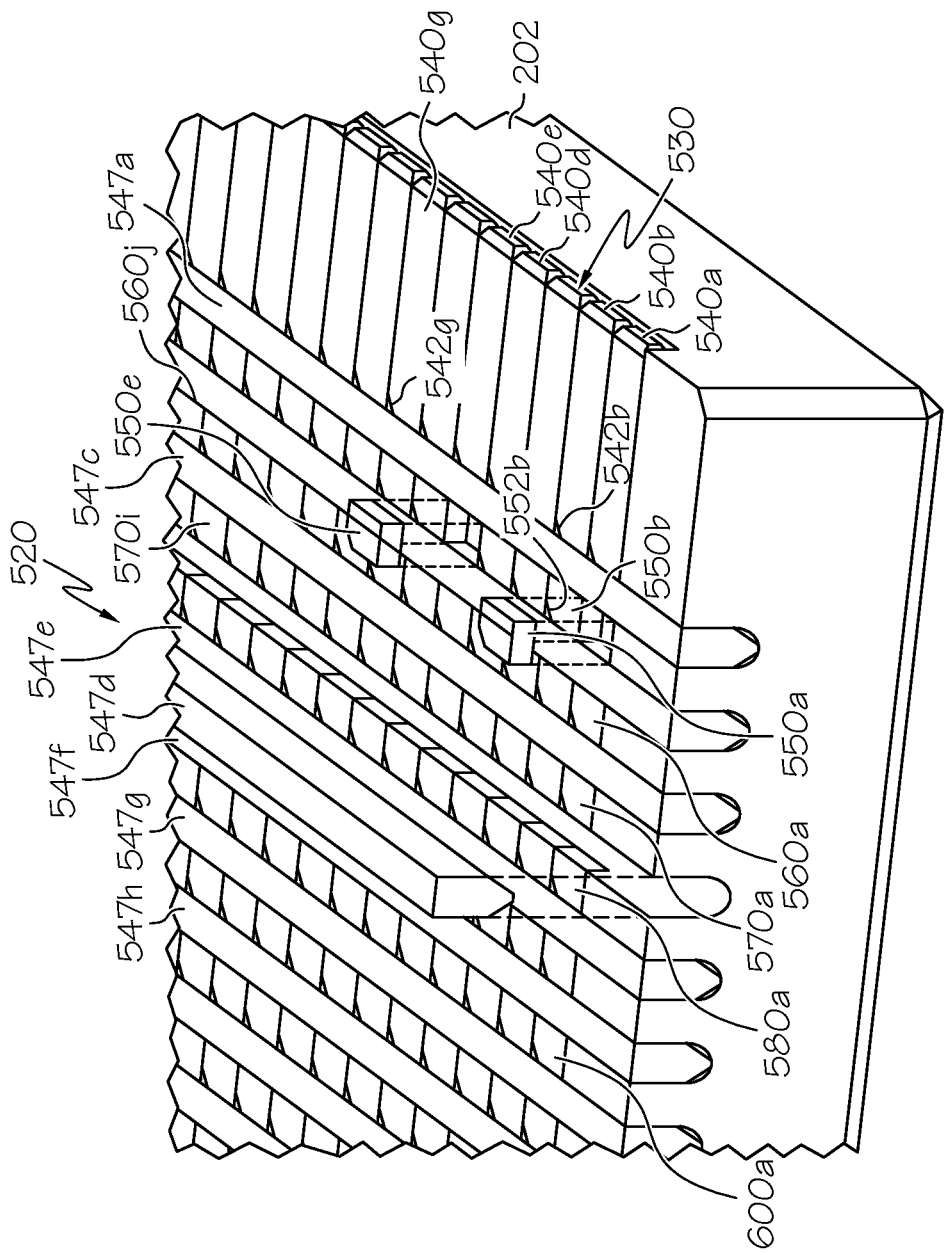
FIG. 19A is a detail of the mold system of FIG. 17.
Figure 19B:
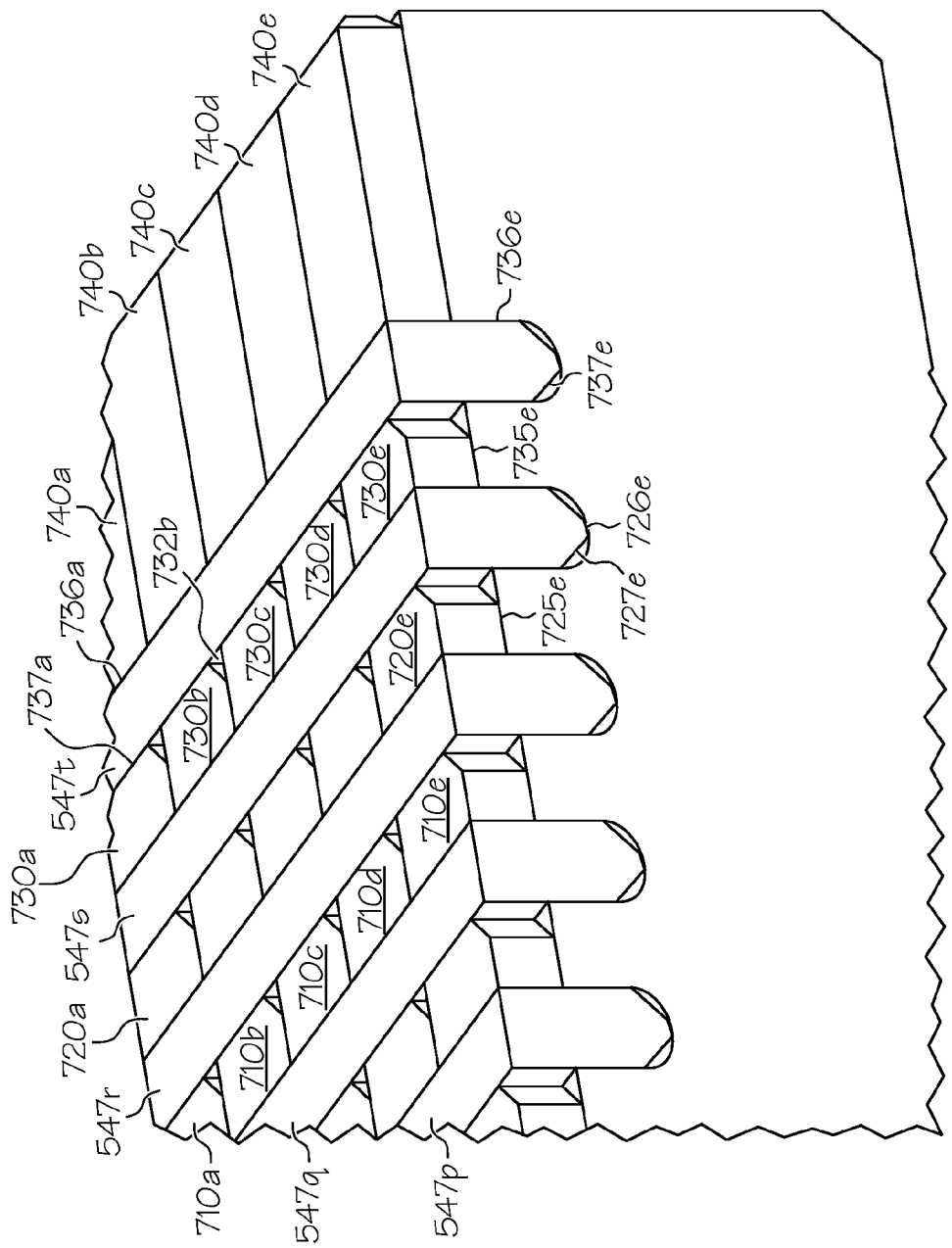
FIG. 19B is a detail of the mold system of FIG. 17.

Referring to FIGS. 17-19, another embodiment of a plastic injection mold system 520 is shown to form a plurality of elements 155. FIG. 18 illustrates one of element 155 that the plurality of elements may comprise. The plastic injection mold system 520 comprises a first cavity mold plate assembly 530 to form a first segment 60 of the element 155 using a plurality of mold cavities 542a-t, 552a-t, 562a-t, 572a-t, 582a-t, 592a-t, 602a-t, 612a-t, 622a-t, 632a-t, 642a-t, 652a-t, 662a-t, 672a-t, 682a-t, 692a-t, 702a-t, 712a-t, 722a-t, and 732a-t and a second cavity mold plate (not shown) to form a second segment 70 of the element 155 using a plurality of mold cavities (not shown). For simplicity and clarity purposes, FIGS. 17, 19A, and 19B only show the first cavity mold plate assembly 530 of the mold system 520. In addition, FIGS. 17, 19A, and 19B show a cavity side mold plate 202 of a conventional plastic injection molding machine (e.g., machine 200 as shown in FIG. 12) in order to illustrate the engagement and connection of the first cavity mold plate assembly 530 with and to such cavity side mold plate 202.

As shown and described in the embodiments set forth above herein, the first cavity mold plate assembly 530 and the cavity side mold plate 202 may form a first transverse intersection 535 as shown in FIG. 19B. Additionally, not to be limited by theory, the first transverse intersection 535 may form a micro edge along transverse edge 66 of the element 155 shown in FIG. 18 due to the gas exiting and/or out-gassing from the plurality of mold cavities as the transverse intersection 535 as shown and described above herein with respect to the embodiments. Similarly, not to be limited by theory, a second transverse intersection (not shown) may be formed between the first cavity mold plate assembly 530 and the second cavity mold plate (not shown) to form a micro edge along transverse edge 76 of element 155 as shown in FIG. 18 due to the gas exiting and/or out-gassing from the plurality of mold cavities as the transverse intersection as shown and described above herein with respect to the embodiments. It should be understood that second transverse intersections may be removed by the first and second segments 60 and 70 from a single and/or integral mold plate having an integral mold cavity that forms both segments. As such, the gas cannot exit and/or out-gas at the place within the mold cavity that forms the transverse edge 76.

As shown in FIGS. 17, 19A, and 19B, the first cavity mold plate assembly 530 may comprise a plurality of individual cavity mold plates (e.g., cavity mold plates 540a-t, 550a-t, 560a-t, 570a-t, 580a-t, 590a-t, 600a-t, 610a-t, 620a-t, 630a-t, 640a-t, 650a-t, 660a-t, 670a-t, 680a-t, 690a-t, 700a-t, 710a-t, 720a-t, and 730a-t), a plurality of plate separators 547a-t, and a plurality of end plates 740a-t. The cavity mold plates and plate separators form a plurality of mold cavities. For example, the cavity mold plates 540a-t and plate separator 547a form a plurality of mold cavities 542a-t, the cavity mold plates 550a-t and plate separator 547b form a plurality of mold cavities 552a-t, the cavity mold plates 560a-t and plate separator 547c form a plurality of mold cavities 562a-t, and so on through the cavity mold plates 730a-t, wherein the cavity mold plates 730a-t and plate separator 547t form a plurality of mold cavities 732a-t.

When assembled, the cavity mold plates (e.g., cavity mold plates 540a-t, 550a-t, 560a-t, 570a-t, 580a-t, 590a-t, 600a-t, 610a-t, 620a-t, 630a-t, 640a-t, 650a-t, 660a-t, 670a-t, 680a-t, 690a-t, 700a-t, 710a-t, 720a-t, and 730a-t) and the plate separators 547a-t form a plurality of first and second longitudinal intersections between these cavity mold plates and the plate separators. As examples, a first longitudinal intersection 737a is formed between cavity mold plate 730a and plate separator 547t, and a second longitudinal intersection 736a may be formed between the cavity mold plate 730b and plate separator 547t as shown in FIG. 19B. Not to be limited by theory, these two longitudinal intersections may form micro edges along longitudinal edges 68b and 68c respectively of mold cavity 732a due to the gas exiting and/or out-gassing through the respective intersections during the plastic injection molding process. As another example, a first longitudinal intersection 737e may be formed between cavity mold plate 730e and plate separator 547t, and a second longitudinal intersection 736e may be formed between the cavity mold plate 730f and plate separator 547t as shown in FIGS. 17, 19A, and 19B. Again, not to be limited by theory, these two longitudinal intersections may form micro edges along longitudinal edges 68b and 68c respectively of mold cavity 732e due to the gas exiting and/or out-gassing through the respective intersections during the plastic injection molding process.

A plurality of third longitudinal intersections may be formed between (i.e., the abutment of) adjacent cavity mold plates 540a-t, 550a-t, 560a-t, 570a-t, 580a-t, 590a-t, 600a-t, 610a-t, 620a-t, 630a-t, 640a-t, 650a-t, 660a-t, 670a-t, 680a-t, 690a-t, 700a-t, 710a-t, 720a-t, and 730a-t. As an example, a third longitudinal intersection 735a may be formed between adjacent cavity mold plates 730a and 730b. Again, not to be limited by theory, this third longitudinal intersection 735a may form a micro edge along the longitudinal edge 68a of mold cavity 732a due to the gas exiting and/or out-gassing through this intersection during the plastic injection molding process. As another example, another third longitudinal intersection may be formed between adjacent cavity mold plates 730e and 730f. Moreover, not to be limited by theory, this third longitudinal intersection 735e may form a micro edge along the longitudinal edge 68a of mold cavity 732e due to the gas exiting and/or out-gassing through this intersection during the plastic injection molding process.

With this configuration, each of the plurality of mold cavities 542a-t, 552a-t, 562a-t, 572a-t, 582a-t, 592a-t, 602a-t, 612a-t, 622a-t, 632a-t, 642a-t, 652a-t, 662a-t, 672a-t, 682a-t, 692a-t, 702a-t, 712a-t, 722a-t, and 732a-t may form a segment of an element 155 having three longitudinal intersections (e.g., 735e, 736e, and 737e) that permit the formation of three longitudinal edges 68a, 68b, and 68c that comprise micro edges as shown and described herein. It is understood that a longitudinal intersection may be formed at each and every abutment of a cavity mold plate 540a-t, 550a-t, 560a-t, 570a-t, 580a-t, 590a-t, 600a-t, 610a-t, 620a-t, 630a-t, 640a-t, 650a-t, 660a-t, 670a-t, 680a-t, 690a-t, 700a-t, 710a-t, 720a-t, and 730a-t with a plate separator 547a-t and between each and every adjacent cavity mold plate as shown in FIGS. 17 and 19.

In the embodiment shown in FIGS. 17-19, when the gas exits/out-gases from the mold cavities at and along these transverse and longitudinal intersections between the cavity mold plates, the gas pushes and/or draws the plastic deep into the corners. In so doing, the molding process of this mold system is able to form micro edges at and along any intersection, both transverse and longitudinal, between two cavity mold plates and/or assemblies, cavity mold plates/assemblies and plate separators, adjacent mold plates, cavity mold plates/assemblies and mold machine surfaces (e.g., cavity side mold plate 202), and/or any combinations thereof.

It is understood that if additional longitudinal edges were desired on both segments 60 and 70, the second cavity mold plate 730 could be divided up into individual cavity mold plates as the first cavity mold plate included, thus forming transverse edges 66 and 76 and longitudinal edges 68a, 68b, 68c, 78a, 78b, and 78c as micro edges. It is also understood that this mold system may be configured to mold any number of segments for the element 50 by adding or subtracting the number of cavity mold plate layers, i.e., if four segments desired, the mold system 520 will include four cavity mold plates. It is also understood that each cavity mold plate layer may comprise the individual cavity mold plates, plate separators, and other components as shown and described above here as well as other relevant modifications. In addition, although a triangular-shaped transverse cross section was shown in the embodiments shown and described above, any transverse cross sectional shape may be used, including different transverse cross sectional shapes for each segment of an element.

Figure 20:
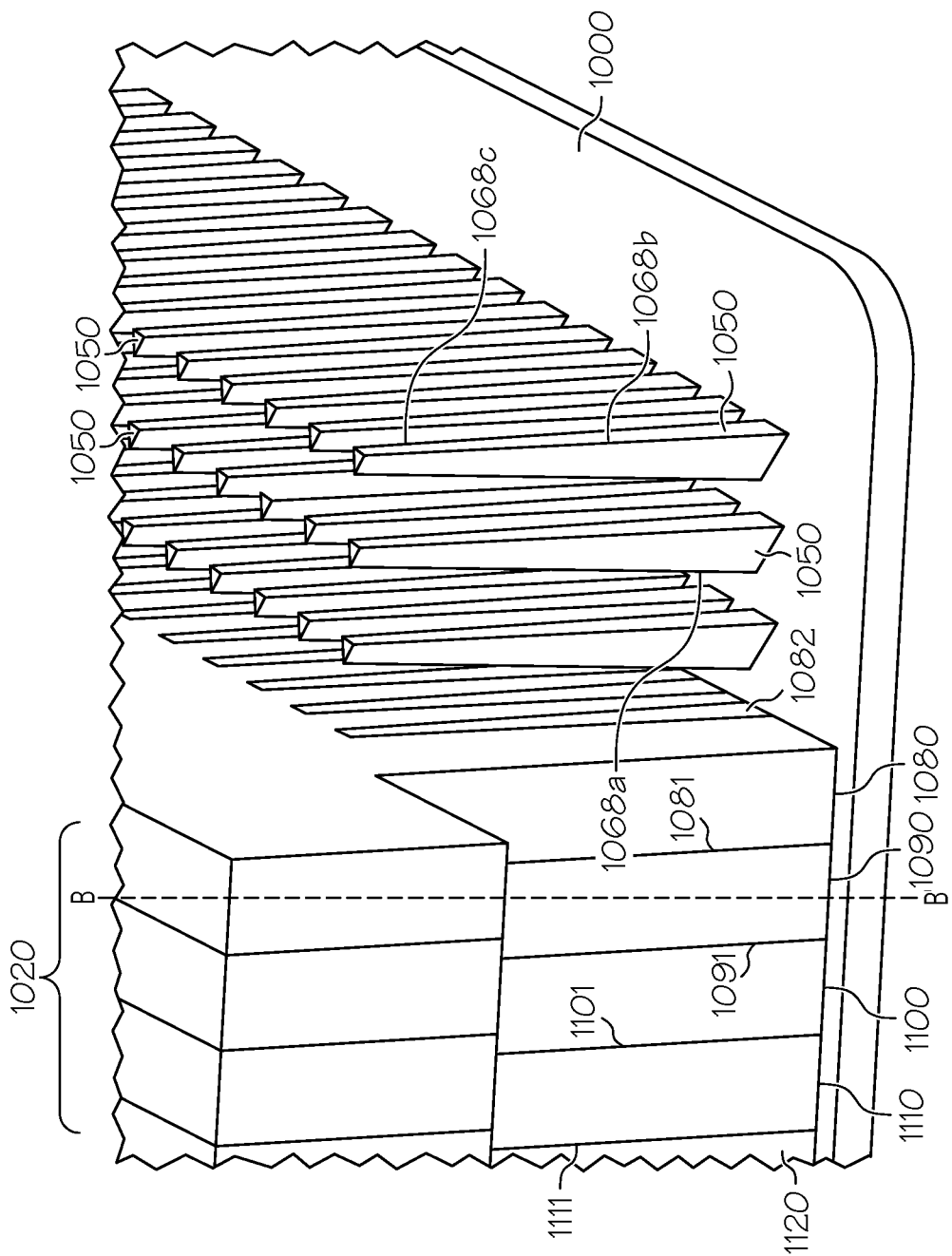
FIG. 20 is a partial perspective view of another embodiment of a mold system.
Figure 21:
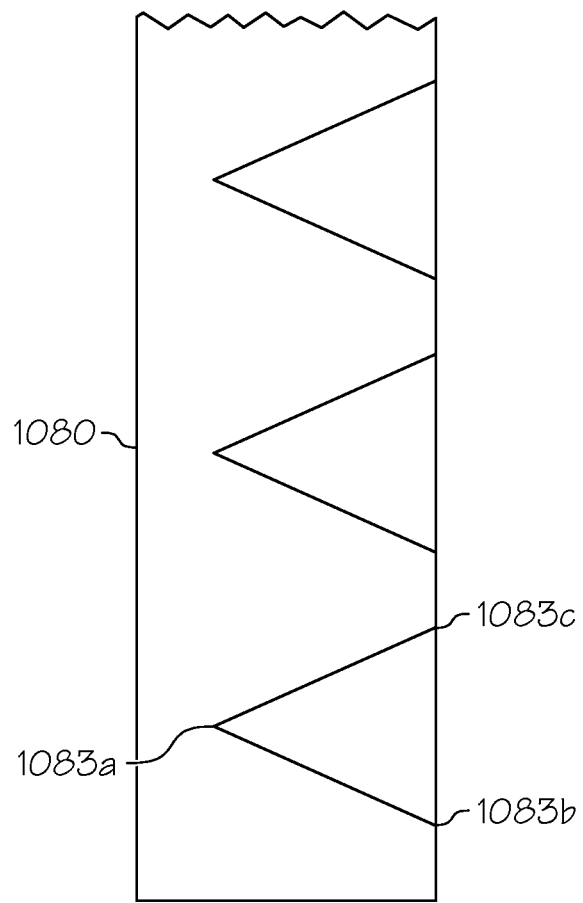
FIG. 21 is a partial cross sectional view of an embodiment of a cavity mold plate of the mold system of FIG. 20.

Referring to FIGS. 20 and 21, another embodiment of a plastic mold system 1020 and elements 1050 that may be molded using such plastic mold system 1020 are shown. The several embodiments of the mold system 1020 may be used with a conventional plastic injection mold machine as shown and described above herein and known to one of ordinary skill in the art (e.g., mold machine 200 shown in FIG. 12). In one embodiment, the mold system 1020 may comprise a plurality of cavity mold plates (e.g., cavity mold plates 1080, 1090, 1100, 1110, 1120, etc.) that are disposed side-by-side in an orientation that is along a longitudinal axis B-B' rather than having the cavity mold plates position upon each other in an orientation transverse to the longitudinal axis B-B' such as, for example, the first, second, third, and fourth cavity mold plates 230, 240, 250, and 260 of the mold system shown in FIGS. 12-14. In the configuration shown in FIGS. 20 and 21, the mold system 1020 would form longitudinal intersections (e.g., longitudinal intersections 1081, 1091, 1101, 1111, etc.) between each of the cavity mold plates (e.g., cavity mold plates 1080, 1090, 1100, 1110, 1120, etc.). As shown in FIG. 20, the mold plates 1080, 1090, 1100, 1110, 1120, etc., are operable to mold a plurality of elements 1050 using a plurality of mold cavities 1082.

As shown in FIG. 20, elements 1050 each comprise longitudinal edges 1068a, 1068b, and 1068c. Referring specifically to FIG. 21, the longitudinal edge 1068a is formed by an internal corner 1083a of the mold cavity 1082. Thus, not to be limited by theory, the longitudinal edge 1068a may not be a micro edge as defined herein because the gas within the mold cavity 1082 may not exit and/or out-gas through this internal corner 1083a because this corner does not comprise an intersection between to mold plates. The longitudinal edge 1068a may comprise a non-out-gassed edge. A "non-out-gassed" edge is an edge of the flexible element that is formed within a single cavity mold plate, i.e., an internal corner within a single mold plate and thus an edge not formed along an intersection of two molding plates, used in a molding process such as plastic injection molding. In other words, a non-out-gassed edge is an edge formed without using out-gassing between and through the intersection of two molding plates. In contrast, the longitudinal edges 1068b and 1068c are formed by mold cavity corners 1083b and 1083c which are formed by a longitudinal intersection between two cavity mold plates (e.g., cavity mold plate 1080 and adjacent cavity mold plate (not shown)). Thus, the longitudinal edges 1068*b* and 1068*c* may be formed as micro edges as defined here.

In one embodiment, a molding cycle for a plurality of cleaning elements and a base unit fabricated from a Pellethane 2363 resin comprises a barrel temperature of from about 380 degrees F. to about 410 degrees F., a mold temperature of from about 60 degrees F. to about 140 degrees F., and an injection pressure of from about 1600 bar to about 1800 bar.

Figure 22:
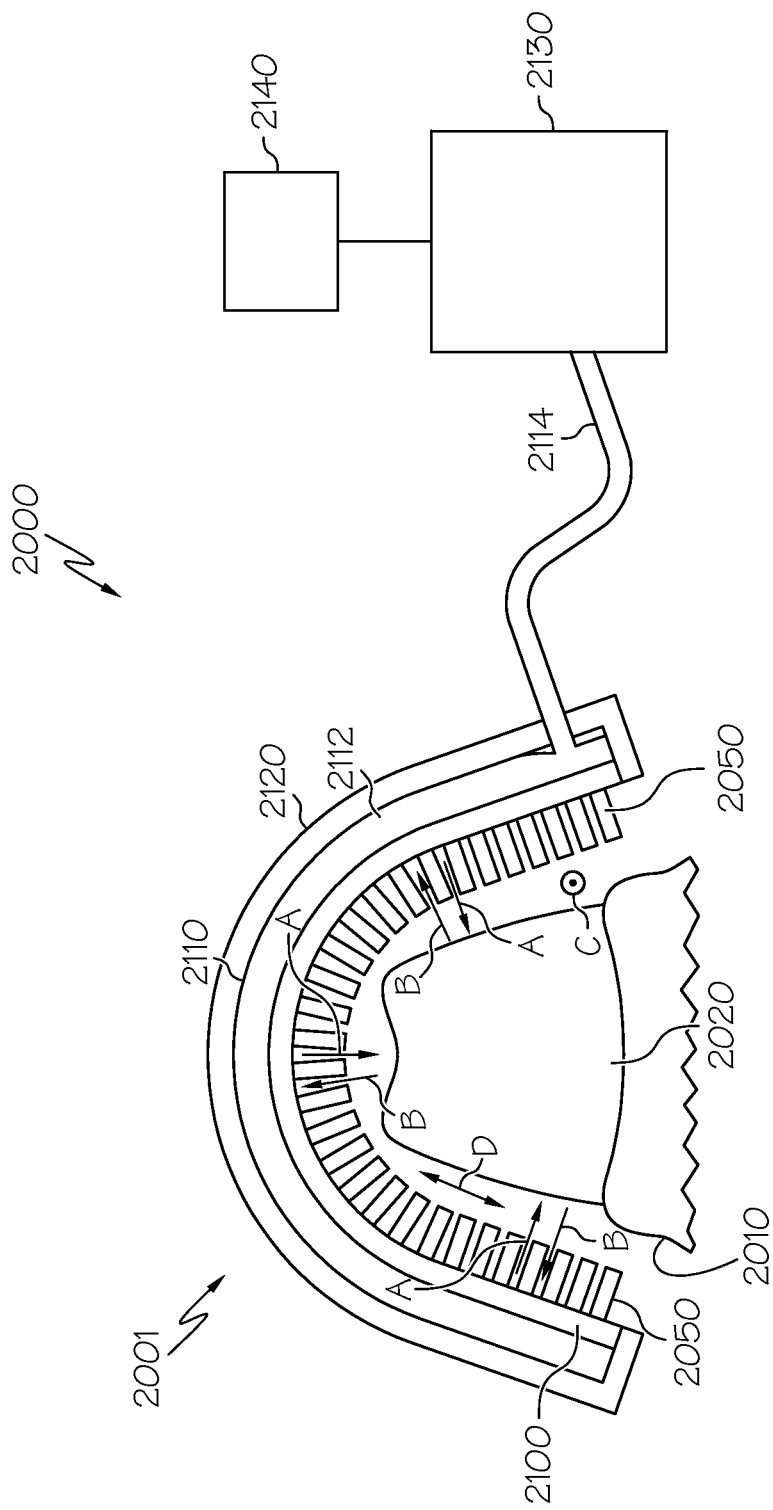
FIG. 22 is a schematic representation of an embodiment of an oral care system.

Referring to FIG. 22, an embodiment of an oral care system 2000 is shown, which may comprise an oral care implement 2001 having a base 2100, a plurality of flexible, elastomeric elements 2050 extending from the base 2100, and a drive system operable to drive, move, and/or push the plurality of flexible, elastomeric elements 2050 and/or the base 2100 such that the plurality of elements 2050 engage teeth 2020 and/or gums 2010 disposed within an oral cavity (e.g., a human mouth). In one embodiment, the plurality of elements 2050, the base 2100, and at least a portion of the drive system is configured to insert into an oral cavity and be positioned adjacent teeth 2020 and gums 2010 of the oral cavity. The oral care system 2000 may further comprise a housing 2120. The base 2100 and plurality of elements 2050 may comprise any of the embodiments shown and described above herein.

As shown in FIG. 22, the drive system may comprise bladder 2110 positioned on a side of the base 2100 opposite the plurality of elements 2050. The bladder 2110 may comprise a reservoir 2112 for receiving a fluid and be flexible such that the bladder may expand and contract in response to fluid filling or emptying from the reservoir 2112. Examples of the flexible materials that the bladder may be fabricated from may include, but not be limited to natural rubber and other sulfur vulcanizable rubbers such as butyl, nitrile, styrenebutediene, saturated rubbers such as silicone, ethylene propylene and epichlorohydrin and thermoplastic elastomers such as polyurethane, polyolefin and styrenic block copolymers. The drive system may also comprise a pump 2130 for supplying a fluid from a fluid source (not shown), a conduit 2114 connecting the pump 2130 to the bladder 2110, and/or a motor 2140 for driving the pump. The pump 2130, conduit 2114, and motor 2140 may comprise any conventional or yet-to-be developed pumps, conduits, and/or motors, particularly such devices that are used for oral care systems. The conduit 2114 may comprise rigid or semi rigid piping or flexible hosing as known to one of ordinary skill in the art.

The oral care system 2000 may pump a variety of known or yet-to-be developed fluids into the bladder 2110 from the fluid source, including but not limited to water, air, gases, any combinations thereof, and other fluids operable to drive the bladder. The source may be a reservoir, the atmosphere, compressed gas tank, or any other conventional fluid supply. The motor 2140 may be a conventional or yet-to-be developed motor, including but not limited to an electric (both D/Cpowered or A/C-powered), magnetic, fuel-powered, manually-powered, electro-chemical, or combinations thereof.

The oral care system 2000 may comprise a housing 2120 that is connected to or integral to the base 2100. In this embodiment, the bladder 2110 is at least partially encompassed by the base 2100 and the housing 2120. The housing 2120 may be fabricated from a semi-rigid or rigid material in order to provide a sturdy structure such that when the bladder 2110 expands due to the reservoir 2112 filling with fluid, the bladder is forced to expand in the direction shown by arrows (A). Examples of the materials used to fabricate the housing 2120 may include, but not be limited to plastics, metals, composites, and combinations thereof. Examples of the plastics that may be used for the housing may include, but not be limited to polyacete polyolefin, polyamide and polyvinylchloride. As the bladder 2110 expands in direction (A) it causes the elements 2050 to engage the teeth 2020 and gums 2010 ("Impact"). The drive system may be reversed as well to cause the base 2100 and/or the elements 2050 to move away from the teeth 2020 and gums 2010 as illustrated by arrows (B). As such, the pump 2130 may draw the fluid from the reservoir 2112 of the bladder 2110, causing the bladder 2110 to contract and thus cause the elements 2050 to move away from the teeth 2020 and gums 2010 ("Lift-off"). The bladder 2110 may comprise a pressure from about 0 kPa to about 60 kPa, particularly from about 10 kPa to about 40 kPa, or more particularly about 20 kPa. Also, the pressure the elements apply to the teeth 2020 and gums 2010 may comprise from about 0 kPa to about 60 kPa, particularly from about 10 kPa to about 40 kPa, or more particularly about 20 kPa.

The drive system may be connected to a controller such as a micro-controller or microprocessor. This controller may be operable to control the motor and/or pump and thus the pumping of fluid into and out of the bladder 2110, causing a reciprocating action of the plurality of elements 2050 against and away from the teeth as illustrated by arrows (A and B). The frequency of the reciprocation of the bladder 2110 and thus the elements 2050 (e.g., between Lift-off and Impact) may be from about 1 Hz to about 100 Hz, more particularly from about 50 Hz to about 90 Hz, more particularly from about 65 Hz to about 75 Hz, or more particularly about 70 Hz. In one embodiment, the plurality of elements 2050 may be moved away from the teeth 2020 and gums 2010 ("Lift off") a distance from about 0 mm to about 10 mm, particularly from about 0 mm to about 8 mm, particularly from about 3 mm to about 7 mm, particularly from about 4 mm to about 6 mm, or more particularly from about 0 mm to about 5 mm. Also, the implements 2050 may be driven back toward the teeth 2020 and gums 2010 ("Impact") a distance from the teeth 2020 and gums 2010 ("Lift off") a distance from about 0 mm to about 10 mm, particularly from about 0 mm to about 8 mm, particularly from about 3 mm to about 7 mm, particularly from about 4 mm to about 6 mm, or more particularly from about 0 mm to about 5 mm.

In another embodiment, the drive mechanism may comprise more than one of the bladder 2110, particularly if desired to drive elements 2050 in different directions. In yet another embodiment, the driving mechanism may cause the plurality of elements 2050 to move along the teeth 2020 and gums 2010 as illustrated by arrows (C), i.e., into and out of the figure and (D), i.e., transverse to arrow (C). The oral care system 2000 and one or more drive systems may cause the elements 2050 to move or oscillate in one or more of the directions along arrows (C) and/or (D) a distance from about 0 mm to about 10 mm, particularly from about 0 mm to about 6 mm, or particularly from about 0 mm to about 4 mm. Instead of a fluid pump and bladder, the drive mechanism may comprise a variety of other conventional and yet-to-be developed drive and/or actuation systems, including but not limited to ultrasonic drives, vibrating drives, oscillating drives, electric motors, piezoelectric, electrostrictive, electromagnetic, magnetostrictive, acoustostrictive, photostrictive and/or chemostrictive actuators.

Figure 23:
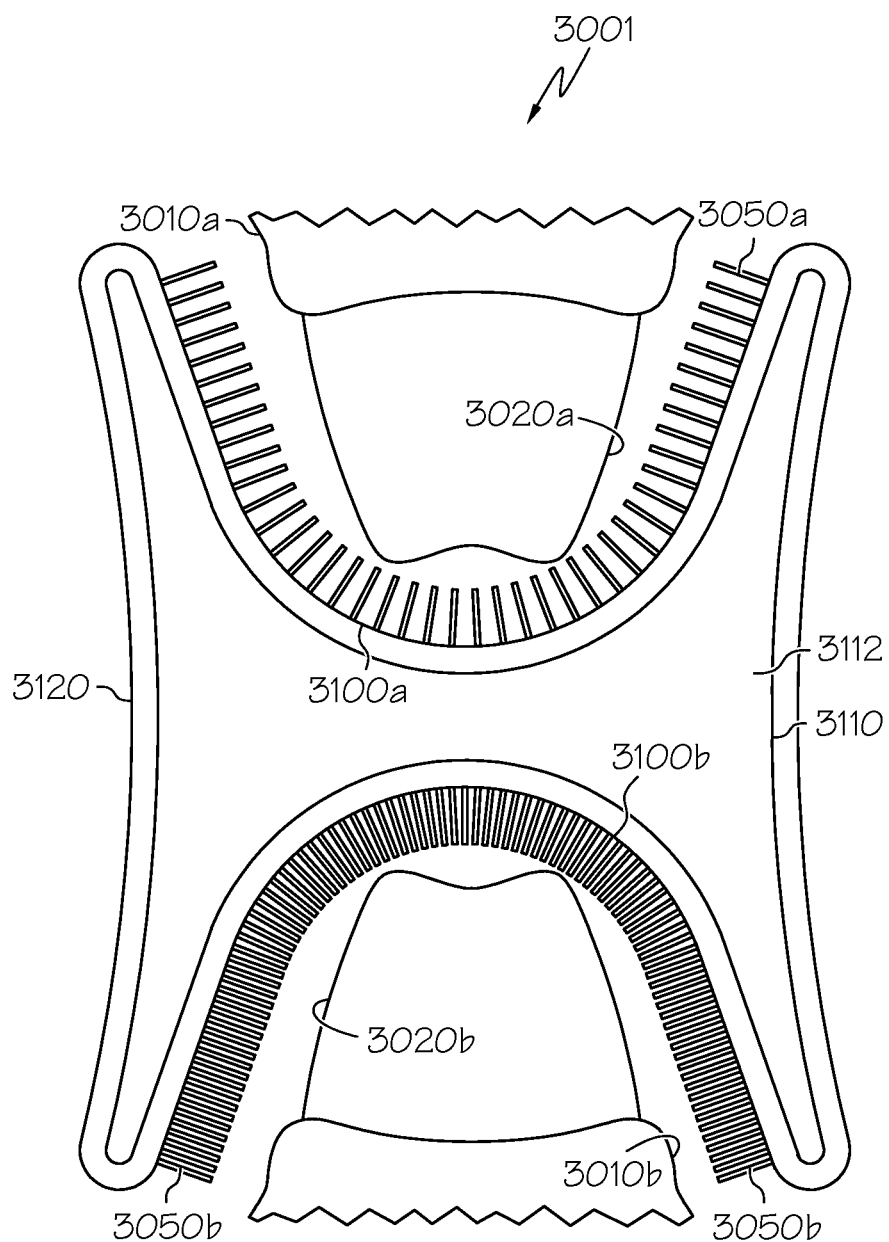
FIG. 23 is a schematic representation of another embodiment of an oral care implement.

In another embodiment, an oral care implement 3001 shown in FIG. 23 may comprise a housing 3120 having a first flexible base 3100*a* connected to the housing 3120, a first plurality of elements 3050*a* extending from the first base, a second flexible base 3100*b* connected to the housing 3120, a second plurality of elements 3050*b* extending from the second base, and a bladder 3110 having a reservoir 3112 therewithin. The oral care implement 3001 is configured to be inserted within an oral cavity and be substantially U-shaped such that the first plurality of elements 3050a and/or first base 3100a substantially conform and/or surround all or some portion of teeth 3020a and/or gums 3010a disposed along the upper jaw and the second plurality of elements 3050b and/or second base 3100b substantially conform and/or surround all or some portion of teeth 3020b and/or gums 3010b disposed along the lower jaw simultaneously. In such a configuration, the oral care implement 3001 is operable to clean the teeth 3020a-b and/or gums 3010a-b of the upper and lower jaws simultaneously, sequentially, or any combination thereof. It is understood that the oral care implement 3001 may be combined with any variety of oral care systems, including but not limited to the several embodiments of the oral care systems shown and described herein (e.g., oral care system 2000).

One or more of the embodiments of the oral care systems (e.g., oral care system 2000) may clean oral cavity tissue (i.e., teeth and gums) in a time less than or equal to about 15 seconds/tooth surface, more particularly less than or equal to about 10 seconds/tooth surface, even more particularly less than or equal to about 5 seconds/tooth surface.

It is also believed, but not intended to be held by theory, that one or more of the embodiments of the oral care systems shown and described herein (e.g., oral care system 2000) and/or oral care implements (e.g., implements 1, 40, 2001) improve interdental (interstitial) cleaning, i.e., cleaning of the teeth and gums disposed between adjacent teeth, compared to conventional oral care cleaning implements and devices. Teeth generally are positioned about 1 mm to about 1.5 mm apart from each other. In one or more of the embodiments shown and described herein, the base (e.g., bases 20, 100, etc.) comprises the plurality of elements spaced (e.g., tip density) such that approximately 6 to 7 elements fit within the space between adjacent teeth (e.g., the approximately 1 mm to 1.5 mm spacing between teeth) thus providing improved interdental cleaning.

Figure 24B:
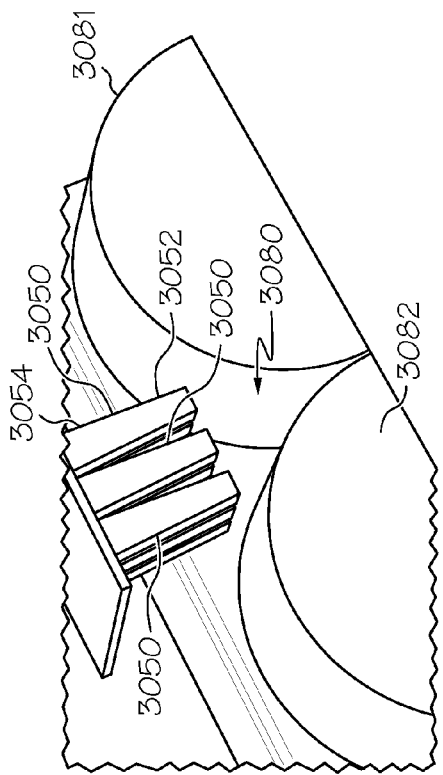
FIG. 24B is a schematic representation of an isometric view of the plurality of flexible, elastomeric elements of FIG. 24A moving into an interdental area of an oral cavity before engagement with any teeth surfaces within the interdental area.
Figure 24A:
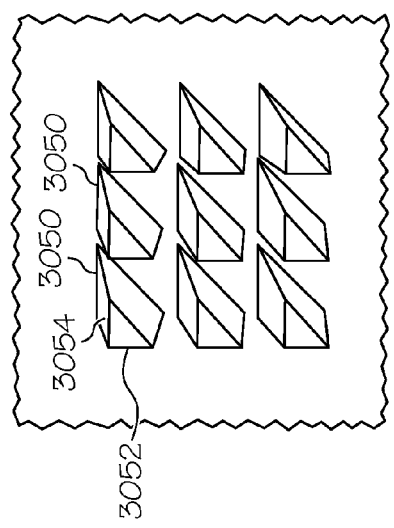
FIG. 24A is a schematic representation of a top perspective view of another embodiment of a plurality of flexible, elastomeric elements.
Figure 24C:
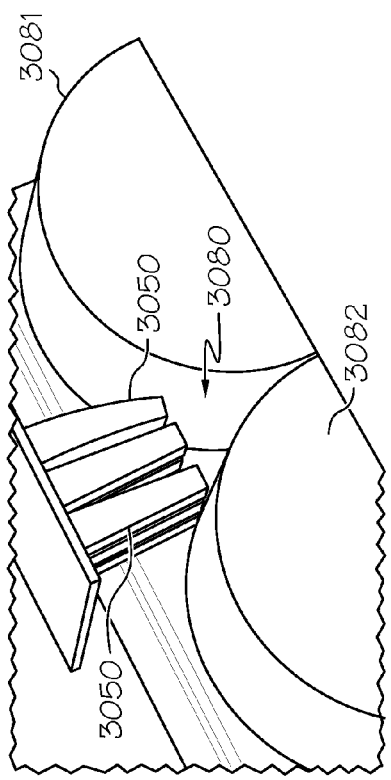
FIG. 24C is a schematic representation of an isometric view of the plurality of flexible, elastomeric elements of FIG. 24A moving into and engaging the interdental area.
Figure 24D:
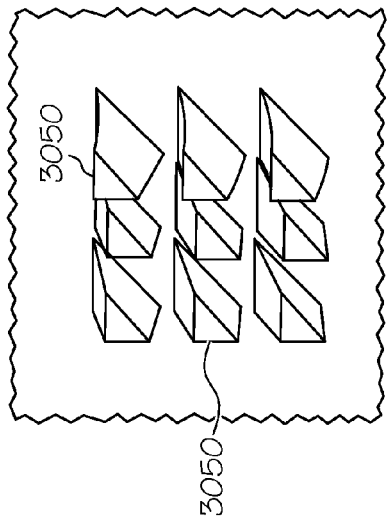
FIG. 24D is a schematic representation of a top perspective view of the plurality of flexible, elastomeric elements of FIG. 24C, illustrating the initial twisting, bending, and/or deformation of the plurality of flexible, elastomeric elements.

As an example, FIGS. 24A-F illustrate such oral care implement having flexible cleaning elements that provide improved interdental cleaning due to the elements size (e.g., width, length) and oral care implement's element density as set forth above. FIGS. 24A-F illustrate sequential frames of an array of flexible elements 3050 having a triangular shape, transverse cross-section as they are moved and/or pushed into an interdental area 3080 between two teeth 3081 and 3082, respectively. Perspective representations of a view from distal ends 3052 toward proximal ends 3054 of the plurality of flexible elements are shown in FIGS. 24A and 24D, and isometric views are shown in FIGS. 24B and 24C to illustrate an example of the orientation and position of the flexible, elastomeric elements 3050 with respect to the interdental area 3080 before and as the plurality of flexible elements 3050 are being moved into and initially engaging the teeth surfaces within the interdental area 3080.

As set forth above and not to be limited by theory, it is believed that the cross-sectional size and shape, length, and/or material properties (e.g., material hardness, material wetness, etc.) of the flexible element along with the element density of the oral care implement and/or the type of motion used to drive the plurality of elements can be utilized and maximized to improve the twisting, bending, and/or other deformation motion of the flexible elements in order to improve and/or maximize the engagement of the edges, particularly micro edges, and the contact stresses with the surfaces of teeth, particularly with the surfaces within interdental areas. FIG. 24 E-F illustrates, as an example, how such a combination of flexible element and oral care implement properties can affect the contact stresses and contact engagement of the edges and/or surfaces of the flexible elements on teeth. As shown, adjusting and controlling such properties will also impact how the flexible elements twist, bend, and/or deform when one or more of the flexible elements fully engage the teeth surfaces within the interdental area 3080.

Figure 24F:
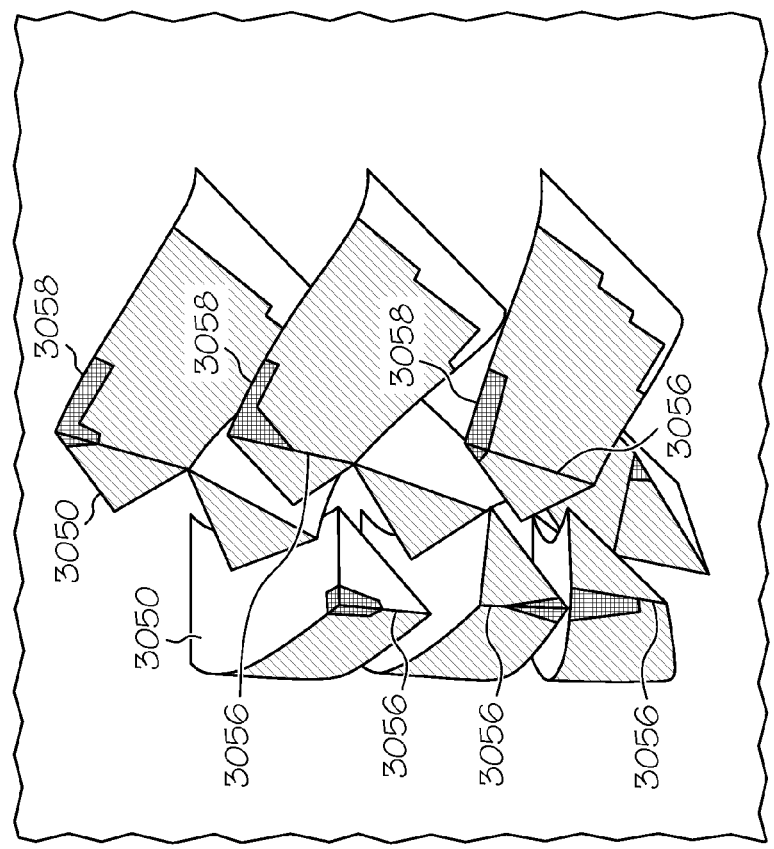
FIG. 24F is a schematic representation of a top perspective view of the plurality of flexible, elastomeric elements of FIG. 24E, illustrating the twisting, bending, and/or deformation of the plurality of flexible, elastomeric elements and contact stresses due to the engagement with the interdental area.
Figure 24E:
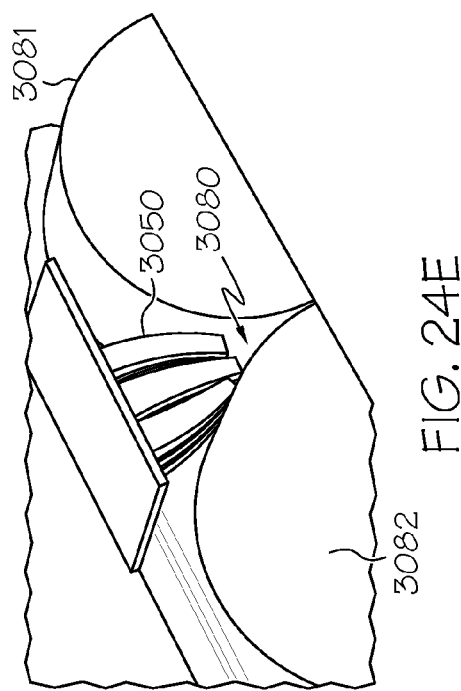
FIG. 24E is a schematic representation of an isometric view of the plurality of flexible, elastomeric elements of FIG. 24D moving further into and engaging the interdental area.

FIG. 24F provides an illustrative representation of a view from the distal ends 3052 toward the proximal ends 3054 shown in FIG. 24E with the teeth removed from the view. As shown in FIG. 24F, one or more of the plurality of flexible elements 3050 twist, bend and/or deform such that more than one transverse edge and/or one or more longitudinal edge are caused to engage the teeth surfaces in the interdental area 3080. It is understood that one or more transverse edge 3056 and/or one or more longitudinal edge 3058 may comprise a micro edge as shown and defined herein. FIG. 24 E also shows, based upon a finite element analysis, via shading what portion of the flexible elements contact the teeth surfaces within the interdental area. The darker shaded areas show the highest level of contact stress (CPRESS in figure legend) between the element and the tooth's surface due to the movement of the element against the tooth. As shown, the configuration in this example provides multiple edges contacting the teeth surfaces (contact trace) with increased contact stresses along those edges, thus providing improved interdental cleaning.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care implement comprising:
    a base portion sized for insertion into an oral cavity; and
    a plurality of flexible, elastomeric elements extending from the base portion; and
    a drive mechanism connected to the base for driving the plurality of flexible, elastomeric elements into engagement with teeth and/or gums within the oral cavity, the drive mechanism including a bladder connected to a side of the base portion opposite the plurality of flexible, elastomeric elements; and
    a fluid source in fluid communication with an interior chamber of the bladder for providing a fluid to the bladder;
    wherein at least one of the plurality of flexible, elastomeric elements comprises
        a first section having a first transverse edge, at least three longitudinal edges and a first transverse cross sectional area, and
        a second section disposed adjacent to the first section along a longitudinal axis of the at least one of the plurality of flexible, elastomeric elements, the second section having a second transverse edge, at least two longitudinal edges and a second transverse cross sectional area different from the first transverse cross sectional area.

2. The oral care implement of claim 1, wherein the second transverse cross sectional area is less than the first transverse cross sectional area.

3. The oral care implement of claim 1, wherein:
the first transverse cross sectional area has a first shape;
the second transverse cross sectional area has a second shape; and
the first shape is different from the second shape.

4. The oral care implement of claim 1, wherein the at least one of the plurality of flexible, elastomeric elements further comprises a third section having a third transverse cross sectional area that is disposed adjacent to the second section along the longitudinal axis, and wherein the third transverse cross sectional area is different than the first and second transverse cross sectional areas.

5. The oral care implement of claim 4, wherein the third transverse cross sectional area is less than the first and second transverse cross sectional areas.

6. The oral care implement of claim 4, wherein the at least one of the plurality of flexible, elastomeric elements further comprises a fourth section having a fourth transverse cross sectional area that is disposed adjacent to the third section along the longitudinal axis of the at least one of the plurality of flexible, elastomeric elements, and wherein the fourth transverse cross sectional area is different than the first, second, and third transverse cross sectional areas.

7. The oral care implement of claim 6, wherein the third transverse cross sectional area is less than the first and second transverse cross sectional areas and the fourth transverse cross sectional area is less than the first, second, and third transverse cross sectional areas.

8. The oral care implement of claim 1, wherein the first and second transverse edges comprise a tip radius (r) that is less than 0.0254 mm.

9. The oral care implement of claim 1, wherein the first and second transverse edges comprise a tip radius (r) that is less than or equal to about 0.015 mm.

10. The oral care implement of claim 1, wherein the first and second transverse edges comprise a tip radius (r) that is from about 0.015 mm to about 0.0015 mm.

11. The oral care implement of claim 1, wherein the plurality of flexible elements are disposed on the base portion such that the base portion comprises an element density from about 0.1 to about 3.0 mm.

12. The oral care implement of claim 1, wherein the first and second transverse edges comprise out-gassed edges.

13. The oral care implement of claim 1, wherein the base portion is substantially U-shaped such that upon insertion into a human mouth, the plurality of flexible, elastomeric elements are adjacent to surfaces of teeth within the mouth.

14. The oral care implement of claim 1, wherein the fluid source comprises a pump and a vacuum for pumping fluid to the bladder and for evacuating the fluid from the bladder.

\* \* \* \* \*